(12) United States Patent
Maclennan

(10) Patent No.: US 10,390,958 B2
(45) Date of Patent: Aug. 27, 2019

(54) ARTIFICIAL INTERVERTEBRAL DISC IMPLANT DEVICE

(71) Applicant: Douglas Stafford Maclennan, Queenscliff (AU)

(72) Inventor: Douglas Stafford Maclennan, Queenscliff (AU)

( * ) Notice: Subject to any disclaimer, the term of this patent is extended or adjusted under 35 U.S.C. 154(b) by 66 days.

(21) Appl. No.: 15/124,346

(22) PCT Filed: Mar. 11, 2015

(86) PCT No.: PCT/AU2015/000139
§ 371 (c)(1),
(2) Date: Sep. 7, 2016

(87) PCT Pub. No.: WO2015/135022
PCT Pub. Date: Sep. 17, 2015

(65) Prior Publication Data
US 2017/0020679 A1    Jan. 26, 2017

(30) Foreign Application Priority Data

Mar. 11, 2014 (AU) ................................ 2014900811
Mar. 19, 2014 (NZ) ........................................ 622352

(51) Int. Cl.
*A61F 2/44* (2006.01)
*A61B 17/70* (2006.01)

(52) U.S. Cl.
CPC .............. *A61F 2/442* (2013.01); *A61B 17/70* (2013.01); *A61B 17/7059* (2013.01);
(Continued)

(58) Field of Classification Search
CPC .......... A61F 2/442; A61F 2/44; A61F 2/4455; A61F 2002/449; A61F 2002/4435;
(Continued)

(56) References Cited

U.S. PATENT DOCUMENTS 6,066,175 A    5/2000 Henderson et al.
6,837,905 B1 *    1/2005 Lieberman ............ A61F 2/4455
606/247
(Continued)

FOREIGN PATENT DOCUMENTS

WO    WO02/085261 A1    10/2002

OTHER PUBLICATIONS

International Preliminary Amendment Report on Patentability dated Feb. 23, 2016, 99 Pages.

*Primary Examiner* — Zade Coley
*Assistant Examiner* — Jessica Weiss

(57) ABSTRACT

An intervertebral disc implant device (10) is arranged to be positioned with respect to at least one disc space that is respectively located between at least two adjacent vertebrae (e.g. C4 & C5). The device comprises a connector (12) that extends between and interconnects the at least two adjacent vertebrae. The device also comprises at least one pad (18) that is integrally formed with and from the same material as the connector to extend laterally therefrom. The at least one pad is configured for location with respect to a respective disc space between the at least two adjacent vertebrae. The material for the pad is continuous from side-to-side, from front-to-back and from a pad top surface to a pad bottom surface. A surgical procedure for deploying the device is also disclosed.

12 Claims, 20 Drawing Sheets

(52) U.S. Cl.
CPC ............ *A61B 17/7061* (2013.01); *A61F 2/44* (2013.01); *A61B 17/7053* (2013.01); *A61F 2002/449* (2013.01)

(58) Field of Classification Search
CPC ............... A61F 2002/443; A61B 17/70; A61B 17/7059; A61B 17/7061; A61B 17/7053
USPC .......................................... 623/17.11–17.16
See application file for complete search history.

(56) References Cited

U.S. PATENT DOCUMENTS

| | | | |
|---|---|---|---|
| 2002/0107571 A1 | 8/2002 | Foley | |
| 2007/0055373 A1* | 3/2007 | Hudgins | ............ A61B 17/7064 623/17.11 |
| 2007/0112428 A1* | 5/2007 | Lancial | ................ A61F 2/4405 623/17.12 |

* cited by examiner

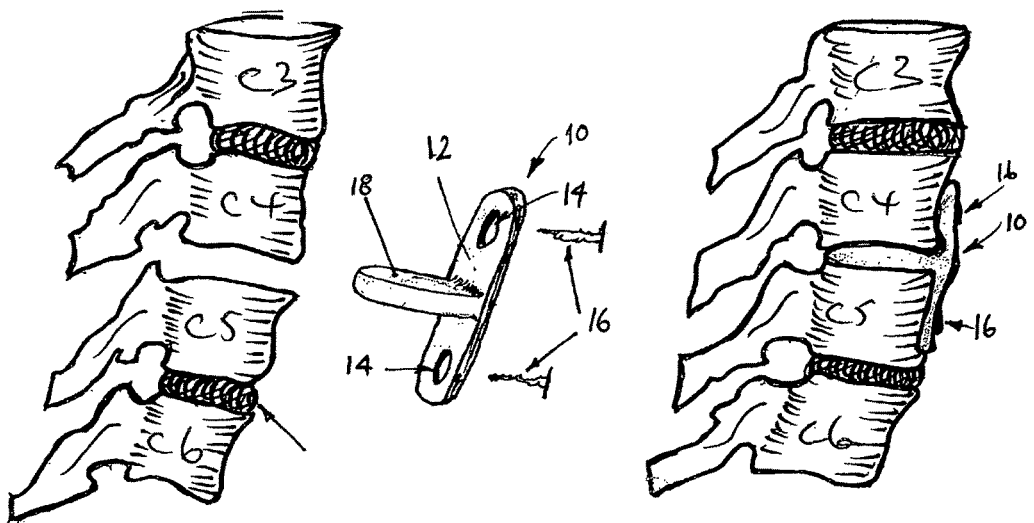
FIG. 3
FIG. 4
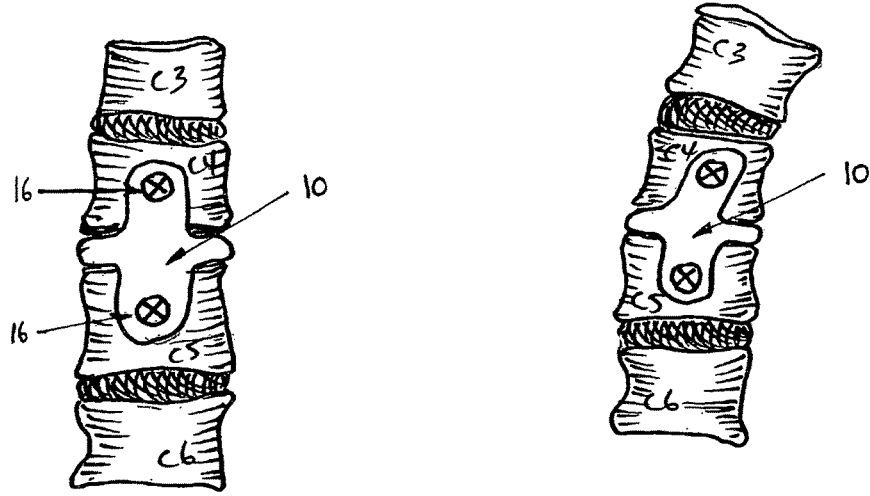
FIG. 5
FIG. 6

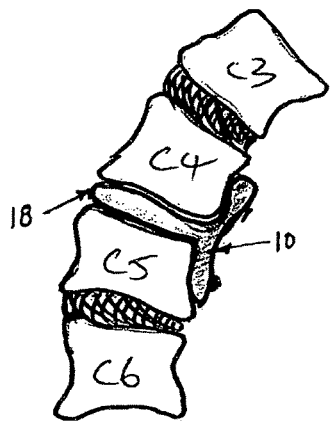
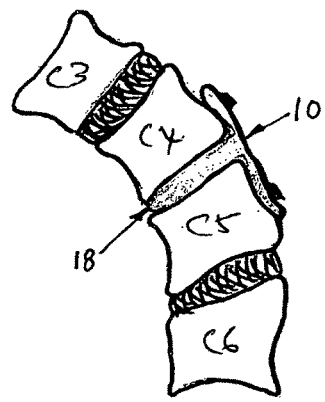
FIG. 7
FIG. 8
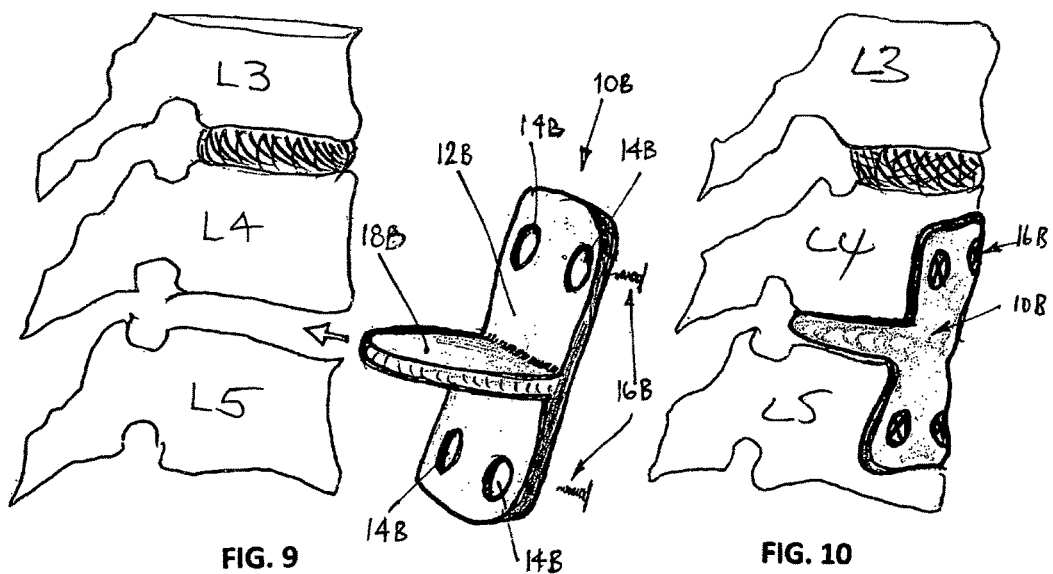
FIG. 9
FIG. 10

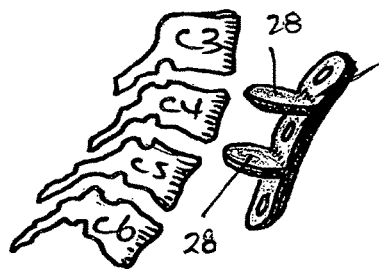
FIG. 19
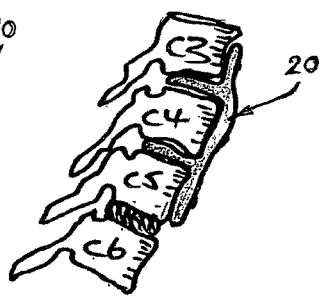
FIG. 20
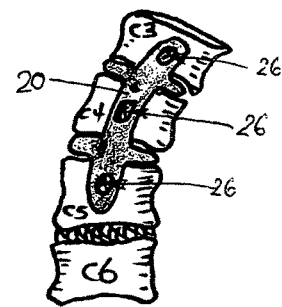
FIG. 21
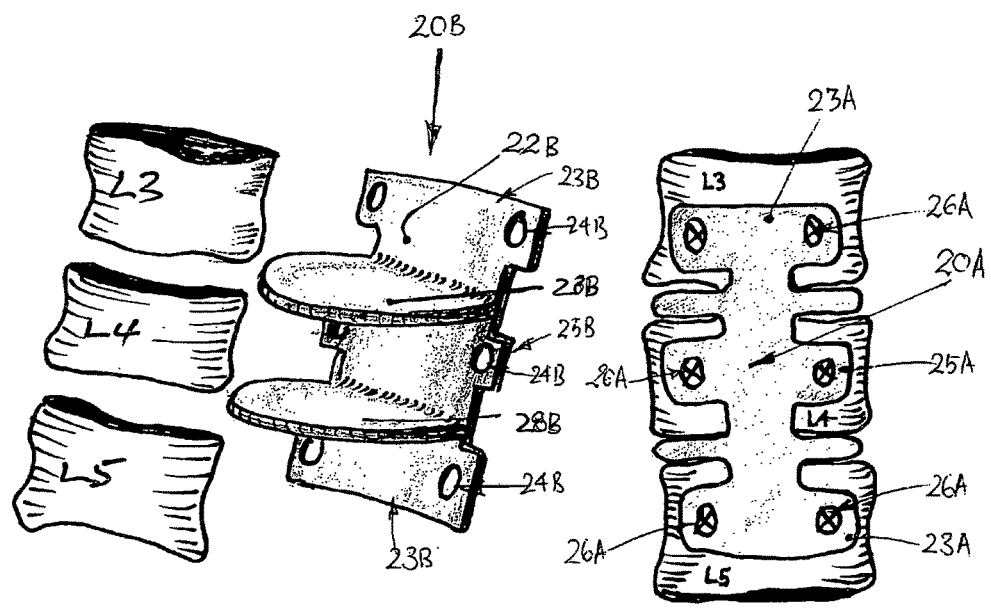
FIG. 22
FIG. 23

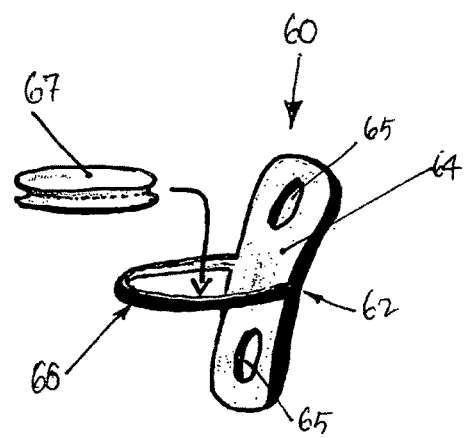
FIG. 28
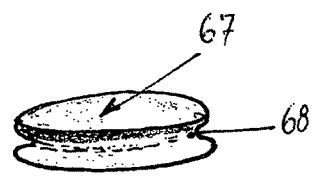
FIG. 29
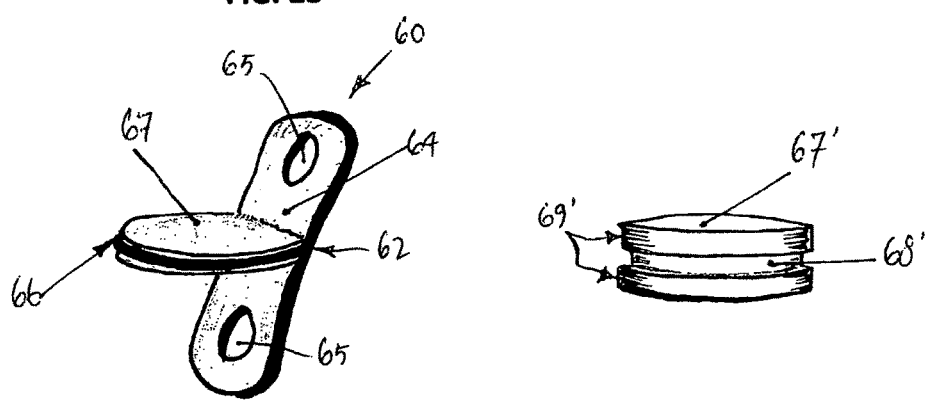
FIG. 30
FIG. 31

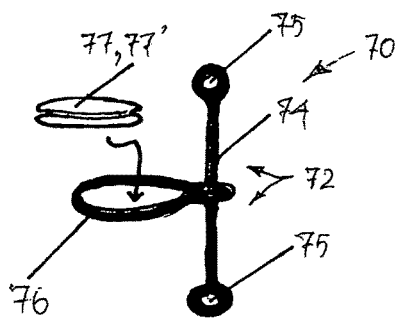
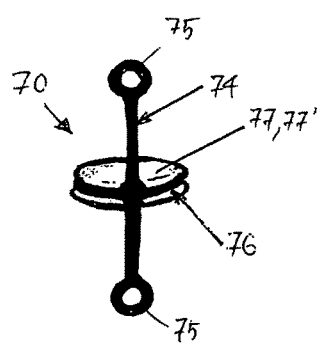
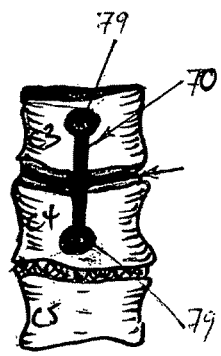
FIG. 32          FIG. 33          FIG. 34
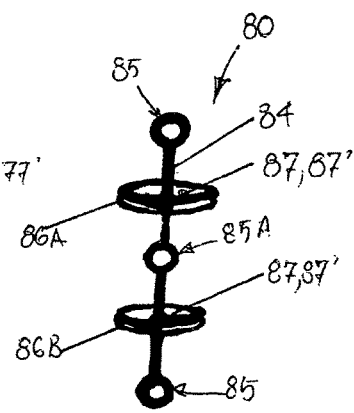
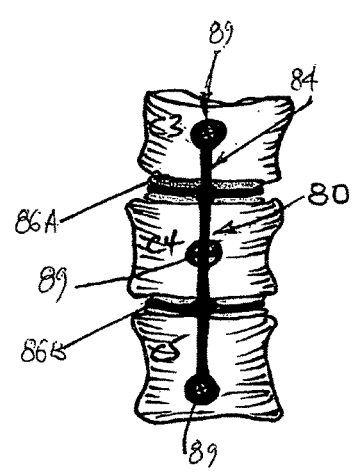
FIG. 35          FIG. 36          FIG. 37

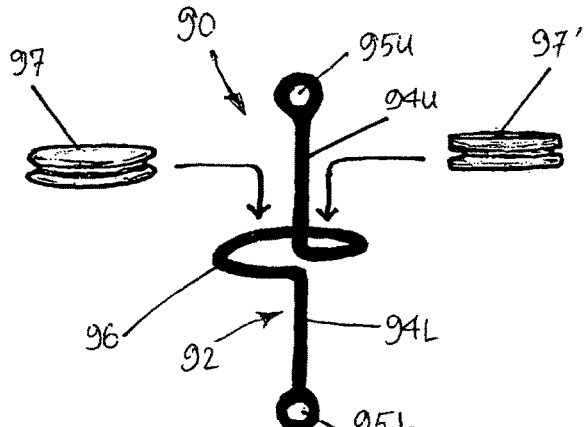
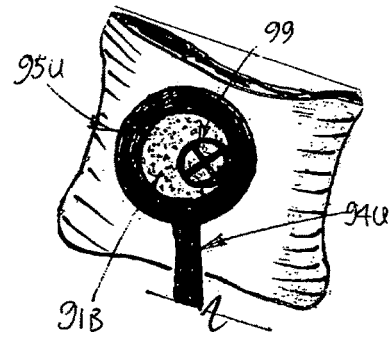
FIG. 38    FIG. 39
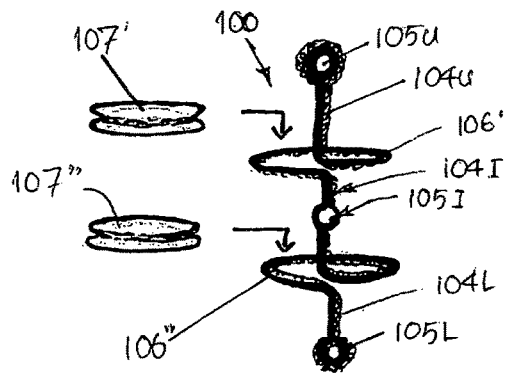
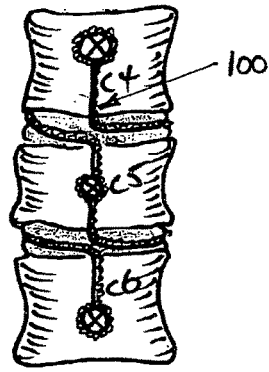
FIG. 40    FIG. 41
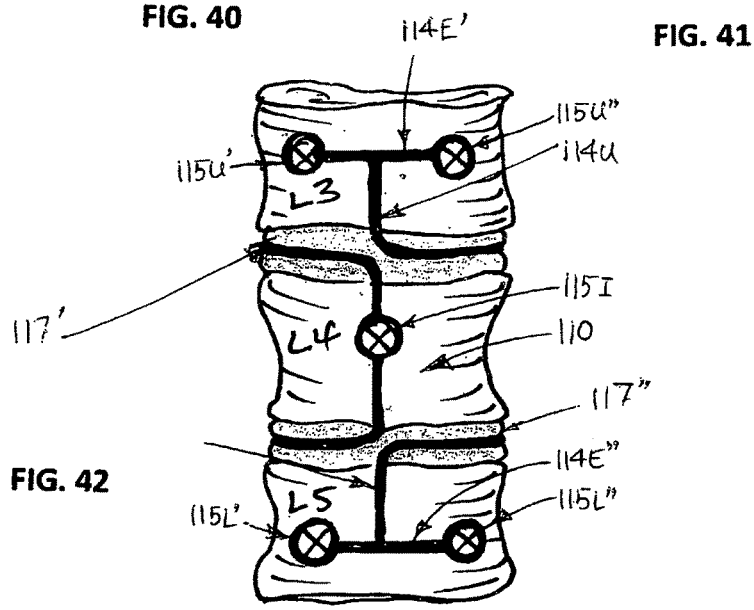
FIG. 42

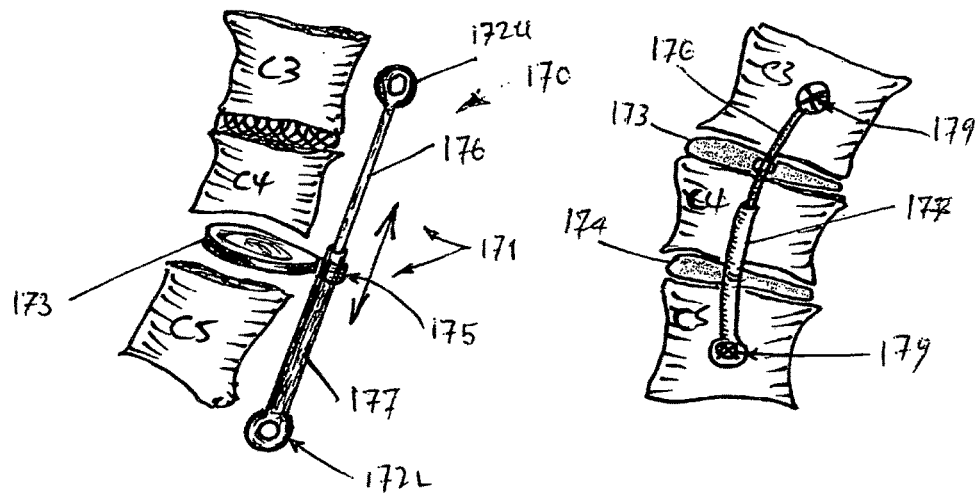
FIG. 51    FIG. 52
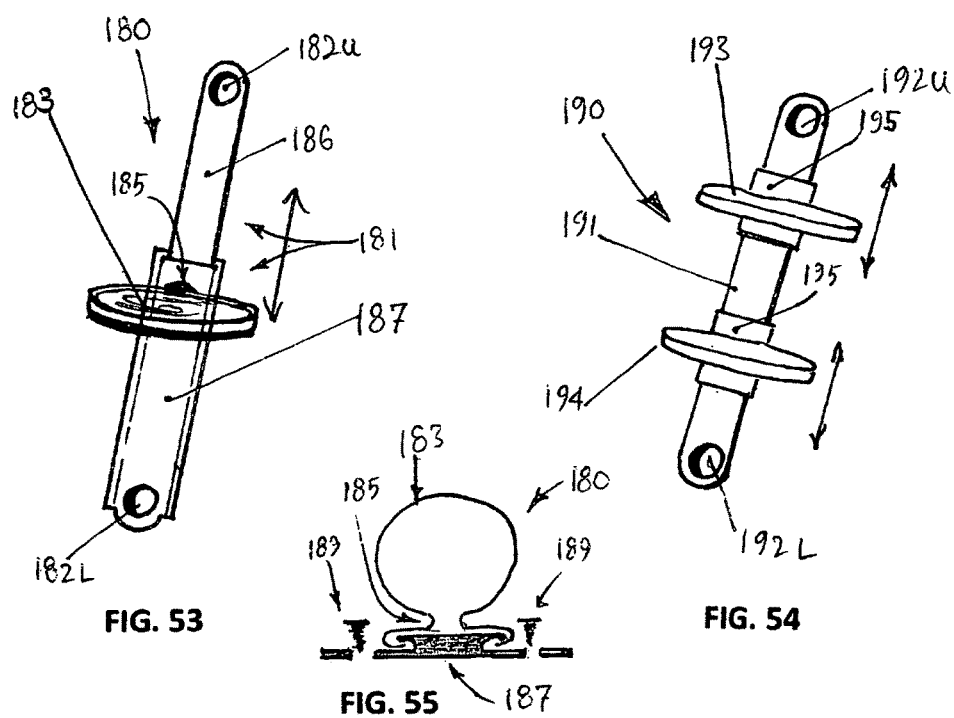
FIG. 53    FIG. 54
FIG. 55

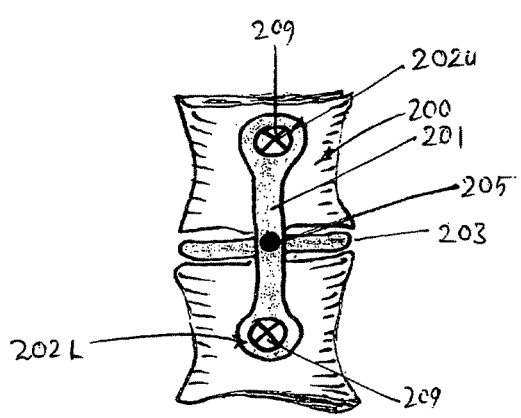 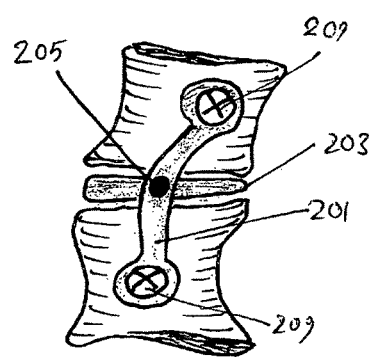
FIG. 56     FIG. 57

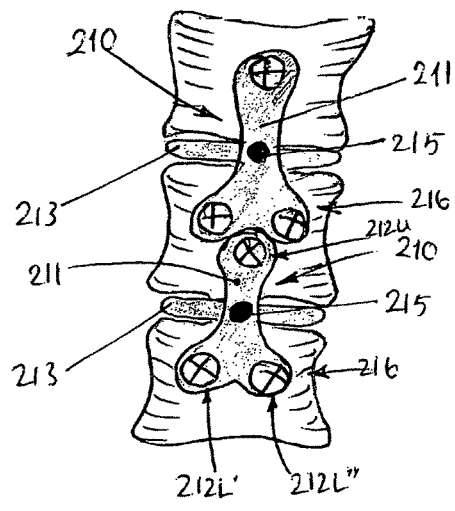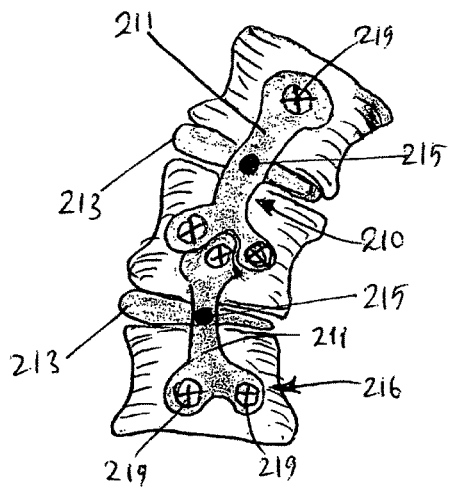
FIG. 58  FIG. 59

ARTIFICIAL INTERVERTEBRAL DISC IMPLANT DEVICE

CROSS REFERENCE TO RELATED APPLICATIONS

This is a National Stage application of PCT/AU2015/000139, filed Mar. 11, 2015, and further claims priority to Australian patent application serial no. 2014900811, filed Mar. 11, 2014, and New Zealand patent application serial no. 622352, filed Mar. 19, 2014, the disclosures of which are incorporated herein by reference.

TECHNICAL FIELD

Disclosed is an artificial intervertebral disc implant device which may be used to replace diseased, prolapsed, fragmented or otherwise damaged intervertebral discs in the spinal columns of humans or animals. A surgical procedure for deploying the device is also disclosed.

BACKGROUND ART

One known surgical technique for correcting intervertebral disc damage or degeneration (and associated instability of the spinal column) involves surgically removing damaged disc material and fusing the vertebrae immediately above and below the damaged disc. In one form, this can be achieved by inserting, anteriorly, a piece or pieces of bone to promote bone grafting in the intervertebral space that previously was occupied by the damaged disc. In another form, this can be achieved by inserting a metallic prosthesis which is so configured and surface-treated such that, when fixed in position between the intervertebral space, new bone growth is more likely to occur. Examples of the latter include the Titan Endoskeleton® suite of devices.

The insertion of bone for the purpose of promoting fusion between adjoining vertebrae may be accompanied by positioning a rigid (e.g. metal) plate across the graft area of the intervertebral disc space and by securing the plate by screws to the anterior face of the vertebrae immediately above and below the graft area. The plate can provide immediate stability to the spinal column at the treated level and can facilitate fusion of the bone graft.

A difficulty with the fusing technique is that anatomical mobility, including rotation at the treated intervertebral level, is not possible. Further, as the number of vertebrae that are fused together increases, the mobility and rotation of the spine is correspondingly reduced. Also, the fusing of two or more vertebrae in this manner may result in increased wear on the discs immediately above and below those which are fused, and this can result in accelerated breakdown of and damage to the discs immediately above and below the fused section. This consequential damage may lead to pain and discomfort for a patient and possibly to further corrective surgery. The rigidity created by fusing a portion of the spinal column, which by nature and function should remain flexible, is not entirely satisfactory. However, it is recognized that in some patients, depending on the extent of their diagnosed intervertebral disc degeneration and or disease, fusing of the vertebrae may be the only surgical option.

Another known surgical technique for correcting intervertebral disc damage or degeneration involves an artificial disc replacement (ADR) device. ADR technologies have been developed to correct or otherwise treat degenerate disc disease (DDD) more effectively and/or as an alternative to fusing techniques. ADR devices are intended to maintain spinal mobility within the normal range of spinal movement and to reduce the incidence of degeneration of discs at adjacent segments of the spine.

Again, the ADR devices are designed to be surgically implanted anteriorly into the intervertebral space between two adjoining vertebrae following surgical removal of the damaged or diseased disc material. The ADR device is intended to function anatomically like a natural disc, ideally maintaining mobility and stability of the spine, and acting ideally as a shock absorber between the vertebrae.

ADR devices that provide for total disc replacement may be composed of metal plates (e.g. titanium, cobalt, chrome) with or without component elements, including materials such as polyethylene, polyurethane, plastics, ceramics, polymers, injectable fluids, hydrogels and elastic coils.

ADR devices are subjected to stringent clinical testing because, among other causes of failure, some ADR devices have been known to dislocate from the intervertebral space between vertebrae.

Examples of spinal disc implants (ADR devices) are shown in each of WO03057088, U.S. Pat. No. 7,066,960, US2009112326, WO2008088869 and KR20100116331.

WO2008088869 discloses a mesh-based spinal implant. Polymer may be moulded around the mesh.

U.S. Pat. No. 7,066,960 discloses a disk prosthesis including a matrix of bio-compatible fabric that is impregnated in its central region with a liquid or semi-liquid polymer to form a nuclear core (nucleus) of the prosthesis.

US2009112326 discloses a spinal implant having first and second flanges, each extending in opposite directions from an intermediate body that comprises upper and lower facing, spaced portions that combine to define an interior in the implant.

WO03057088 discloses a spinal disc implant which comprises an enclosure for insertion into a disc space between two adjacent vertebrae. The enclosure surrounds and supports a plurality of elongated members in the form of polymer rods or tubes.

KR20100116331 discloses an intervertebral cervical spinal implant that has a protruding member extending from a body of the device. However, the protruding member has an annular shape and thereby defines a hollow interior. As a result, saw-tooth projections from upper and lower surfaces of the protruding member are required to abut and interface with the two adjacent vertebrae. KR20100116331 is actually concerned with variable directional fasteners.

The above references to the background prior art do not constitute an admission that such art forms a part of the common and/or general knowledge of a person of ordinary skill in the art. The above references are also not intended to limit the application of the device and procedure as disclosed herein.

SUMMARY OF THE DISCLOSURE

Disclosed herein is an artificial intervertebral disc implant device that is arranged to be positioned and implanted in at least one disc space that is respectively located between at least two adjacent vertebrae in the spinal column in either humans or animals.

The device as disclosed herein comprises a connector for spanning and for interconnecting the at least two adjacent vertebrae.

The device as disclosed herein also comprises at least one pad that is integrally formed with and from the same material as the connector to extend laterally therefrom.

Further, the at least one pad is configured for location with respect to a respective disc space between the at least two adjacent vertebrae.

In contradistinction to prior art implants, the device as disclosed herein is formed such that the material for the pad extends continuously from side-to-side, from front-to-back and from a pad top surface to a pad bottom surface. In other words, the material that is employed for both the connector and the pad defines, in the device, a continuous intervertebral insert, which is able to provide continuity of support between adjacent vertebrae (i.e. having no hollows, gaps, etc).

Thus, the implant device as disclosed herein is able to provide a simple (e.g. able-to-be-moulded/printed in a single stage) device that is also less likely to fail (i.e. which equates with a high level of reliability), due to a simple yet robust construction, and in comparison to more complex prior art implants.

Use herein of the terminology "device" is not intended to imply apparatus that comprises no moving parts. In addition, the terminology is not intended to imply apparatus that does not comprise additional parts.

The device can be deployed, for example, for surgical insertion into any intervertebral disc space and may be fixed to adjoining vertebral bodies of the spinal column. The device, when implanted and when fixed in position, may restore or may otherwise provide adequate stability, flexibility and/or mobility to the treated vertebrae, within the normal range of movement.

The device may be constructed in various sizes, depending upon the position within the spinal column in which a given such device is to be located. For example, an intervertebral disc replacement device that is intended to be positioned within the cervical region will have a size that is smaller than that of an appropriate intervertebral disc replacement device that is intended to be inserted in the thoracic or lumbar regions.

In this regard, a selection of various sizes of the device can be on-hand during a surgical procedure for the surgeon to choose from to match the anatomical size and shape of the vertebrae of different patients. Alternatively, the device may be custom formed in accordance with pre-operative assessment prior to surgery, following for instance the results of a MRI and/or other diagnostic technologies.

In one embodiment, the connector may comprise a reinforcing element extending therethrough. The reinforcing element may comprise a relatively rigid, but bendable, material. For example, the reinforcing element may be of metal (e.g. a surgical steel rod or wire). The reinforcing element may also extend through the pad.

In an embodiment, the connector and optionally pad may be reinforced with a single strand metal wire or a multi-stranded metal wire.

In one embodiment, the connector may be elongate. The connector may be configured at or adjacent to opposing ends thereof to be secured to anterior surfaces of the at least two adjacent vertebrae. For example, the connector may be configured at or adjacent to its opposing ends to be screwed or pinned to the anterior surfaces of the at least two adjacent vertebrae.

In one embodiment, the connector may be sufficiently elongate as to span at least three adjacent vertebrae. In this embodiment the connector may be configured to be secured to the anterior surfaces of each of the at least three adjacent vertebrae. Further, the device may comprise a pad for each of the disc spaces that are respectively located between the at least three adjacent vertebrae.

In an embodiment, the connector may be configured to permit relative displacement of the at least two adjacent vertebrae with respect to each other in use. For example, the connector may be configured to permit rotational and/or pivotal displacement of the at least two adjacent vertebrae with respect to each other in use.

In an embodiment, the connector and pad may be formed from a relatively flexible and yet resilient material.

In an embodiment, the pad of the device may have a disc-shape.

The pad and connector may be formed from a resilient and/or compressible material. Such a material may exhibit mechanical properties similar to those of biological intervertebral discs of the spinal column in which the device is to be employed. For example, the pad and connector may be formed from a compressible yet still resilient material such as a silicon based polymer, a polyaryl-ether-ether-ketone or like plastic. Alternatively, the pad and connector may be formed from rigid or relatively rigid non-compressible material such as a known bio-compatible high density polyurethane or high density polyethylene, or like plastic. Other rigid or compressible polymers may be employed as appropriate.

Also disclosed herein is an intervertebral disc implant device comprises a connector for extending between and for interconnecting the at least two adjacent vertebrae. The device also comprises at least one pad element that is connected to the connector so as to be longitudinally adjustable along the connector. The at least one pad element is configured for location with respect to a respective disc space between the at least two adjacent vertebrae.

The at least one pad element can define a locator for receipt of, or for connection to, a pad. The locator may provide a supporting "framework" to which a separate pad (e.g. such as set forth above) can be secured/mounted/located.

The locator may be integrally formed with (e.g. from the same material as) the connector. Further, when integrally formed, it may comprise a lateral extension of the connector that is arranged for locating in the vicinity of the disc space being surgically treated.

The locator may alternatively be integrally and/or structurally joined to the connector in use. When integrally joined, the locator can be joined to the connector so as not to move laterally with respect to the connector in use. Further, when structurally joined to the connector, the locator can be structurally configured so as to be slidable along the connector in use.

The locator may be configured to connect to a side of the pad. Additionally, or alternatively, the locator may be configured to receive, surround and support the pad therein in use.

The locator may comprise an interconnecting shank. The shank may connect at one end to a side of the pad and/or to a support ring that locates at a circumference of the pad. Further, the shank may have a formation at the other end for connecting to the connector. The formation may allow for the aforementioned slidable movement along the connector in use, but can be such as to not allow lateral movement with respect to the connector in use.

The locator can be configured such that, when the pad is located thereat, the pad protrudes above and below the locator so as to preferentially engage the two adjacent vertebrae in use.

In an embodiment, the connector may comprise a single strand metal wire or a multi-stranded metal wire. The wire may be further configured such as to provide at least one locator for receipt of an insert pad.

When the pad element takes the form of a locator, a pad that is located by the locator may be provided with a peripheral groove defined in its side wall. This groove can be configured to receive therein the single strand or multi-stranded wire.

The pad of the device, whether of compressible or rigid material, may be configured for having an adhesive introduced therethrough so as to enable the pad to be affixed to adjacent one or both of the vertebrae in use. For example, the pad may be configured for the adhesive by providing a small lateral (radial) fluid flow passage that extends inwardly from its periphery to intersect with a generally central small transverse passage. The transverse passage may extend and open at respective top and/or bottom pad surfaces that locate adjacently to one or both of the vertebrae in use of the pad The entire device may be moulded (e.g. injection-moulded), or produced using additive manufacturing techniques, such as by 3D printing using bio-compatible materials. Examples of suitable biomaterials include silicon-based flexible polymers; polysulfones; polypropylene; polyvinylchloride; polytetrafluoroethylene; other fluoropolymers having high biocompatibility for use in medical applications; polyarylether-etherketones; natural rubber latex; synthetic rubbers; elastomers and elasto-plastics; etc. The device may be formed (e.g. printed) at a surgical site, using a 3D scan of a patient's affected vertebra, so as to be specifically designed for an individual patient's vertebra.

Also disclosed herein is a surgical procedure that comprises inserting an intervertebral disc implant device as set forth above between at least two selected and adjacent vertebrae in the spinal column.

In such a procedure, at least a part, if not all, of a diseased, prolapsed, fragmented or otherwise damaged intervertebral disc may first be surgically removed from the spinal column of the patient, before inserting the device. For example, the surgical procedure may comprise:

surgically accessing the at least two selected and adjacent vertebrae of the patient;

removing damaged natural disc from between the at least two selected and adjacent vertebrae;

inserting the pad between the at least two selected and adjacent vertebrae to implant the device;

securing the connector to the anterior faces of the at least two selected and adjacent vertebrae.

BRIEF DESCRIPTION OF THE DRAWINGS

Notwithstanding any other forms which may fall within the scope of the device and procedure as set forth in the Summary, specific embodiments will now be described, by way of example only, with reference to the accompanying drawings in which:

FIGS. 3 to 8 show various in-use views of the implant of the first embodiment of FIG. 1;

FIGS. 9 and 10 show in-use views of another variation on the implant of the first embodiment;

FIGS. 19 to 21 show various in-use views of the implant of the second embodiment of FIG. 16;

FIGS. 22 and 23 show in-use views of a variation on the implant of FIG. 18;

FIG. 28 shows a diagrammatic perspective view of a fourth embodiment of a device in the form of a simple implant, in disassembled format, and formed so as to enable interchange of a pad, in the pad locator;

FIG. 29 shows a diagrammatic perspective view of an interchangeable pad for interchangeable use in the pad locator which is integrally formed with the implant, as depicted in FIGS. 28. and 31;

FIG. 30 shows a diagrammatic perspective view of a variation on the pad of FIG. 29, with the pad depicted in FIG. 29 being composed of compressible but resilient material and the pad in FIG. 30 being composed of rigid non-flexible material;

FIG. 31. shows a diagrammatic perspective view of a fourth embodiment of a device in the form of a simple implant in assembled format, and formed so as to enable interchange of a pad, in the pad locator;

FIGS. 32 and 33 respectively show diagrammatic perspective views of a fifth embodiment of a device in the form of a wire implant which defines a structural framework, in disassembled and assembled formats, and formed so as to enable interchange of a pad, FIG. 34 showing the wire implant of FIGS. 32 and 33 in use with e.g. the cervical vertebrae;

FIG. 35 shows a diagrammatic perspective view of a variation on the wire framework of FIGS. 32 and 33, showing the implant and the pad locator formed from multi-strand wire and with the implant of FIG. 35 in an assembled format;

FIGS. 36 and 37 respectively show assembled and in-use views of another variation on the wire framework, with the implant of FIGS. 36 and 37 being formed or fabricated to span and be affixed to three adjacent vertebrae;

FIGS. 38 and 39 respectively show diagrammatic perspective and detail views of a sixth embodiment of a device in the form of a wire implant which defines a structural framework that is formed so as to enable interchange of a pad;

FIGS. 40 and 41 respectively shows a diagrammatic perspective view of an implant variation on that of FIGS. 38 and 39, the implant comprising a multi-pad locator and being formed from multi-strand wire, with FIG. 41 showing the implant of FIG. 40 spanning and affixed to three adjacent (e.g. cervical) vertebrae;

Figure 1:
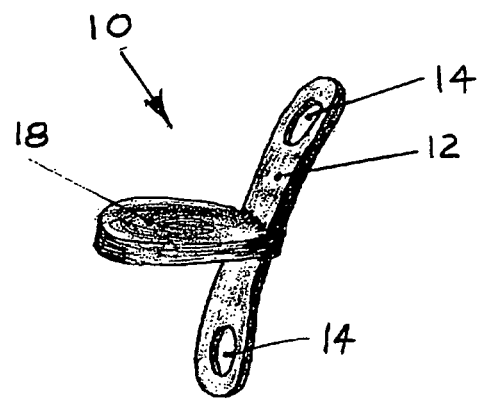
FIG. 1 shows a diagrammatic perspective view of a first embodiment of a device in the form of a simple bracket for use with e.g. the cervical vertebrae.
Figure 43:
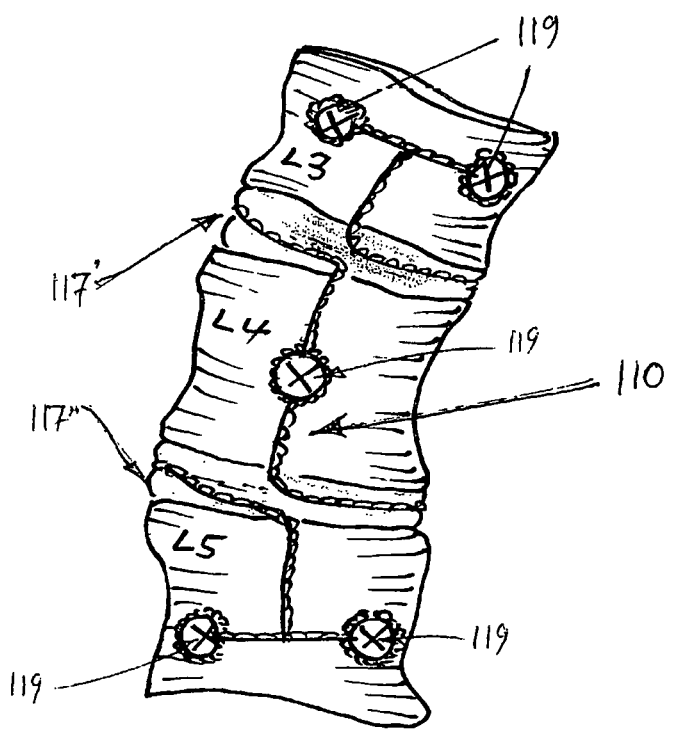
Figures 44, 45:
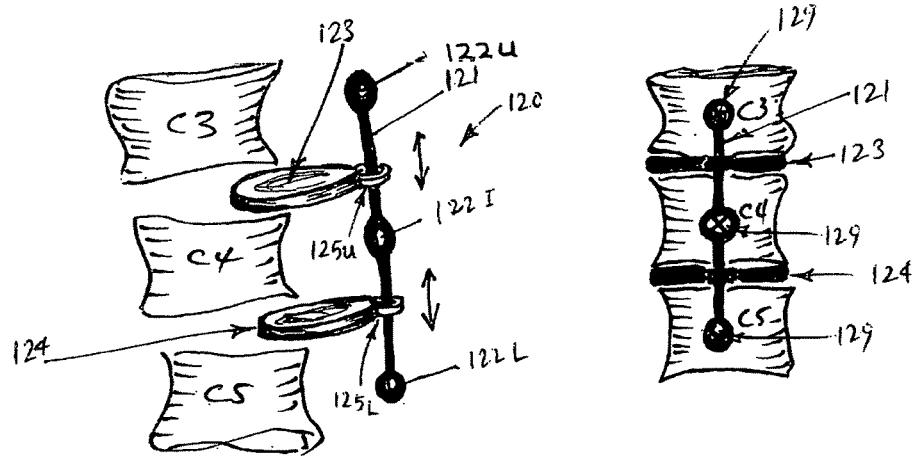
Figures 46, 47:
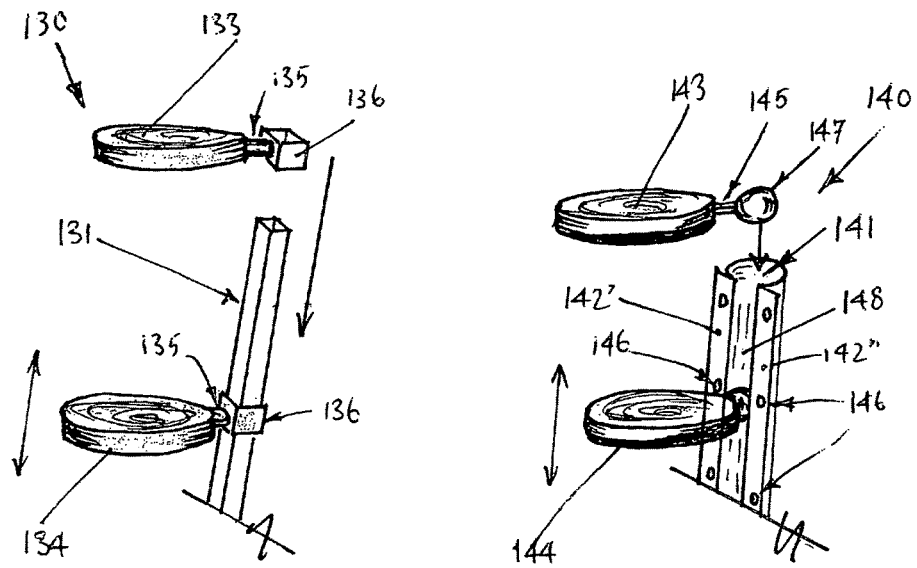
Figure 48:
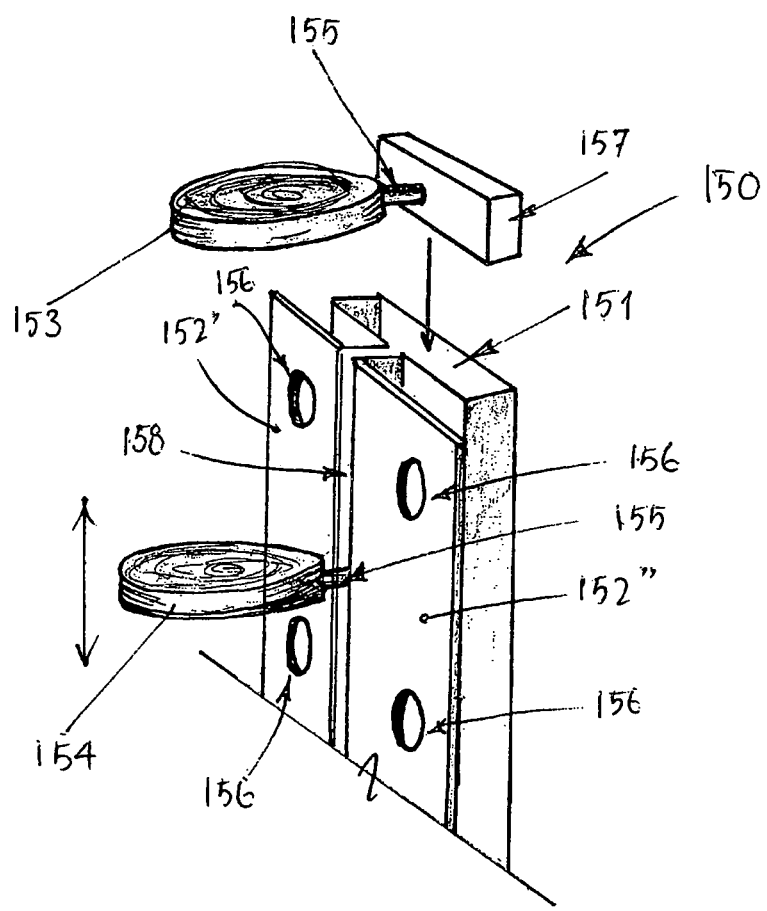
Figure 49:
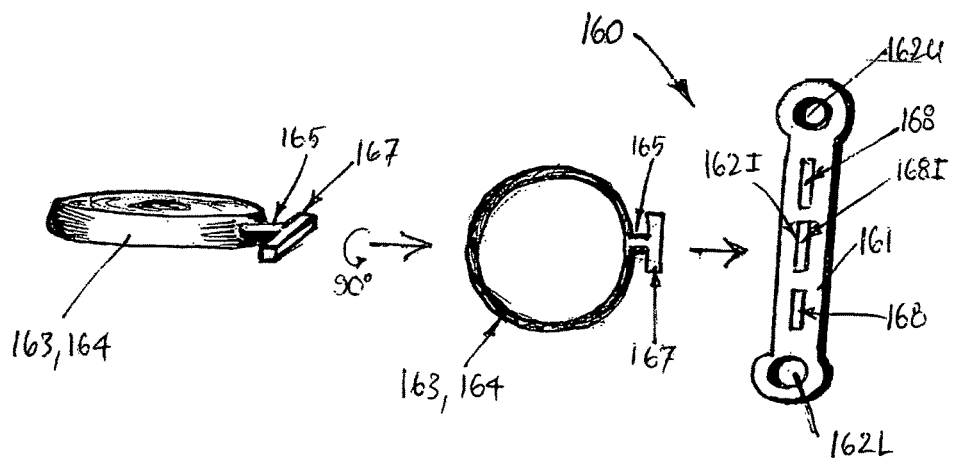
Figure 50:
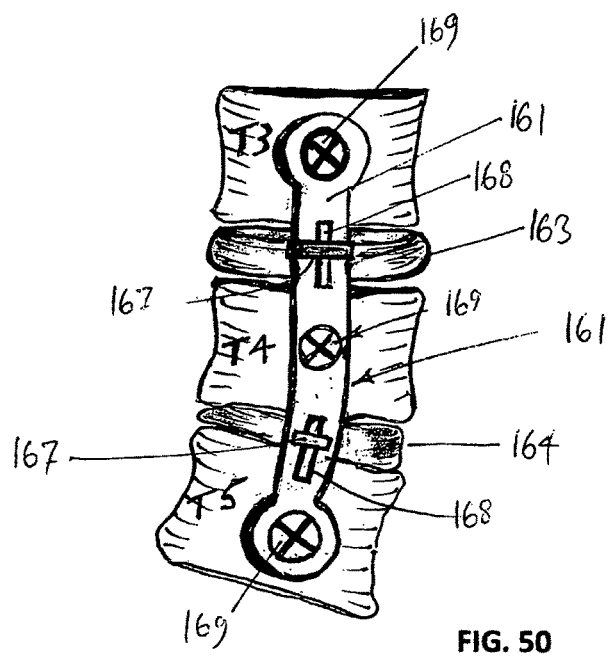
Figure 60:
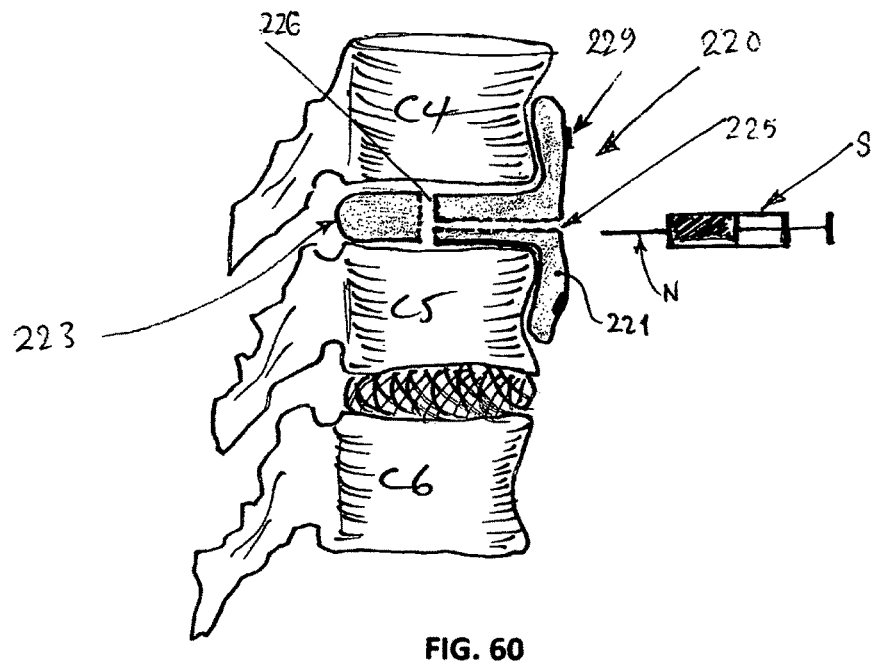
Figure 61:
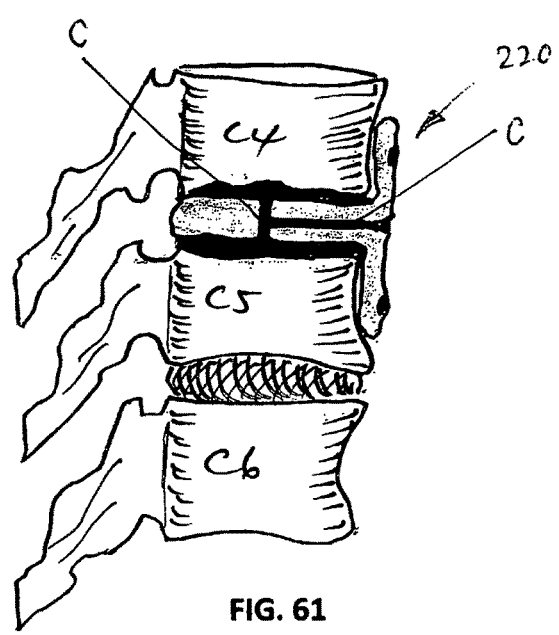
Figure 68:
Figure 69:
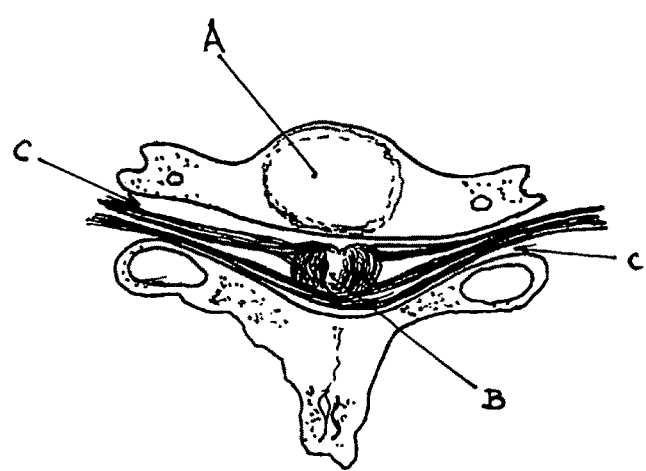

FIGS. 42 and 43 respectively shows a diagrammatic perspective view of another implant variation on that of FIGS. 40 and 41, with FIG 42 made from single strand wire and FIG. 43 from multi-strand wire, both implants shown in situ (i.e. spanning and affixed to three adjacent (e.g. lumber vertebrae), the implant also comprising a multi-pad locator, with the implant of FIG. 43, showing spinal flexion;

FIGS. 45 and 45 respectively show diagrammatic perspective and front views of a seventh embodiment of a device in the form of a wire implant in situ (i.e. spanning and being affixed to three adjacent (e.g. cervical) vertebrae, the implant defining a structural framework that enables in-use vertical displacement of one or more pads;

FIG. 46 shows a diagrammatic perspective view of an implant variation on that of FIGS. 44 and 45;

FIG. 47 shows a diagrammatic perspective view of another implant variation of that of FIGS. 44 and 45;

FIG. 48 shows a diagrammatic perspective view of yet another implant variation of that of FIGS. 44 and 45;

FIGS. 49 and 50 respectively show diagrammatic perspective views of an eighth embodiment of a device in the form of an implant comprising a key-hole multi-pad connection, the implant in FIG. 50 shown in situ (i.e. spanning and being affixed to three adjacent (e.g. thoracic) vertebrae);

FIGS. 51 and 52 respectively show diagrammatic perspective views of a ninth embodiment of a device in the form of an implant comprising a telescopic bracket, the implant shown in situ in FIG. 52 (i.e. spanning and being affixed to three adjacent (e.g. cervical) vertebrae;

FIGS. 53 and 54 respectively show diagrammatic perspective views of implant variation of that of FIGS. 51 and 52;

FIG. 55 shows a diagrammatic perspective cross-sectinal view of the sliding members of the implant variations shown in FIGS. 53 and 54;

FIGS. 56 and 57 respectively show diagrammatic perspective views of a tenth embodiment of a device in the form of an implant comprising a pivot connection of the pad to a bracket of the implant, the implant shown in situ (i.e. spanning and being affixed to two adjacent vertebrae);

FIGS. 58 and 59 respectively show diagrammatic perspective views of an eleventh embodiment of a device in the form of an implant comprising a pivot connection of the pad to a bracket of the implant, the implant further having a configuration at one end of the bracket that allows for dove-tailing of an adjacent like implant, and each implant shown in situ (i.e. spanning and being affixed to three adjacent vertebrae);

FIGS. 60 and 61 respectively show diagrammatic perspective views of a twelfth embodiment of a device in the form of an implant similar in general configuration to the implant of FIG. 1, but comprising transverse, intersecting passages therethrough for the introduction of adhesive/bone-growth promoter, the implant shown in situ (i.e. spanning and being affixed to two adjacent vertebrae);

FIGS. 62 to 68 show various diagrammatic perspective views of insertable pad embodiments for use with devices in the form of implants that are similar in general configuration to the implants of FIGS. 28 to 43; and FIG. 69 shows a cross-section of a typical cervical vertebra showing the circular nature of the disc space (A), normally occupied by a natural disc, and its disposition in respect to the spinal cord (B) and the foraminal nerve exit routes (C).

DETAILED DESCRIPTION OF SPECIFIC EMBODIMENTS

In the following detailed description, reference is made to accompanying drawings which form a part of the detailed description. The illustrative embodiments described in the detailed description, depicted in the drawings and defined in the claims, are not intended to be limiting. Other embodiments may be utilised and other changes may be made without departing from the spirit or scope of the subject matter presented. It will be readily understood that the aspects of the present disclosure, as generally described herein and illustrated in the drawings can be arranged, substituted, combined, separated and designed in a wide variety of different configurations, all of which are contemplated in this disclosure.

A number of different specific embodiments of artificial intervertebral disc implant devices will now be described with reference to FIGS. 1 to 69. Such devices may be implanted in the disc area of a spine, for example, as shown in FIGS. 3 and 4.

After describing the different specific embodiments of the artificial intervertebral disc implant devices, a non-limiting example of a surgical implant methodology will be provided with reference to an Example.

Embodiment 1—Single Disc Replacement Implant (FIGS. 1-15)

A first device embodiment in accordance with the present disclosure comprises an implant having a simple form for replacement of a single and dual degenerated natural discs (this embodiment and its variations are shown in FIGS. 1 to 15). Such an implant may be particularly suited to being produced using an additive manufacturing technique such as 3D printing using bio-compatible materials.

In this embodiment the device takes the form of an implant 10. The implant 10 comprises a connector in the form of an elongate flexible connecting bracket 12 for spanning and for interconnecting two adjacent vertebrae (e.g. C4 and C5, L4 and L5, etc).

More particularly, and as shown in FIG. 1, the connecting bracket 12 is sized to extend between, and is adapted for interconnecting, the two adjacent vertebrae (e.g. the cervical segments of the spine such as the vertebrae C4 and C5 as shown in FIGS. 4-6).

In this regard, apertures 14 are provided in opposite ends of the connecting bracket 12 and through each of which a surgical fastener 16 (e.g. a surgical screw) can be introduced to affix and thereby secure that end to the anterior face of a given one of the adjacent vertebrae.

The implant 10 also comprises a pad in the form of an integrally formed flexible pad 18 (e.g. moulded at the same time as bracket 12, in the same mould cavity). The integrally formed pad 18 is configured for location with respect to a respective disc space between the at least two adjacent vertebrae (see e.g. FIGS. 3-8; FIGS. 9 & 10; FIGS. 11-15).

The pad 18 has a disc-like shape and profile and is formed from a material that is biocompatible and exhibits mechanical properties similar to those possessed by biological intervertebral discs. In this regard, when the pad 18 is formed from the same homogeneous, flexible, resilient and compressible material as the bracket 12, a bio-polymer, such as a silicon-based bio-polymer, can be employed.

The material for the pad 18 extends continuously. In this regard, the material for the pad 18 extends from side-to-side (i.e. from one lateral side as shown in FIG. 1, etc to the other lateral side), from front-to-back (i.e. from where the pad 18 connects to bracket 12 out to its free/remote end, as shown in FIG. 1, etc), and from a pad top surface (i.e. as shown in FIG. 1, etc), to a pad bottom surface (i.e. the underside surface of the pad as shown in FIG. 1, etc).

In other words, the one-and-same material that is employed for both the bracket 12 and the pad 18 defines a continuous intervertebral implant 10, and is thus able to provide continuity of support between adjacent vertebrae. When a suitable material is used, the implant 10 can be easily formed (e.g. moulded or printed) and yet be robust and reliable.

As indicated by FIGS. 6 to 8, by integrally forming the pad 18 with the bracket 12, the implant 10 can enable and facilitate rotational, lateral and pivotal movements of the two adjacent vertebrae with respect to each other in use, within the normal range of spinal movement, and in a manner that simulates the function and mobility of a natural healthy spine. In this regard, FIG. 6 shows implant 10 secured in position between vertebrae C4 and C5 and facilitating spinal flexion to the left; FIG. 7 shows forward flexion; FIG. 8 shows a spinal extension backwards.

Because the connecting bracket 12 interconnects the two adjacent vertebrae, and because the pad 18 is integrally formed with the bracket, the pad can also be better secured within the disc space and thereby prevent unwanted movement of the pad (e.g. dislocation or lateral movement from the intervertebral space between the vertebrae).

Figure 2:
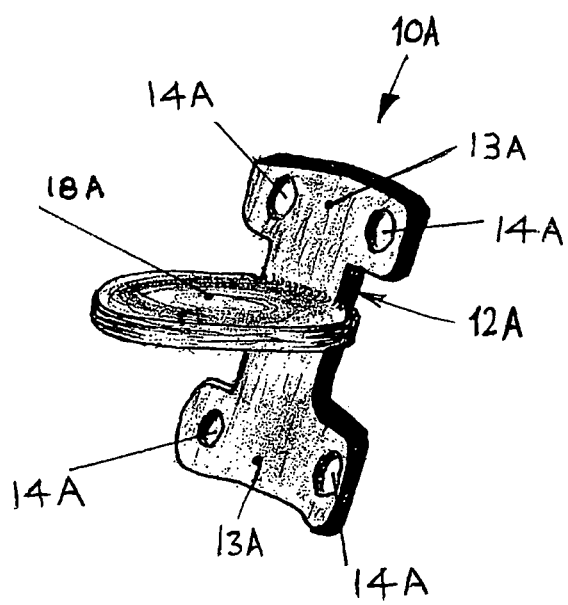
FIG. 2 shows a diagrammatic perspective view of a variation on the implant of the first embodiment of FIG. 1, typically for use with e.g. the lumbar or thoracic vertebrae.
Figure 12:
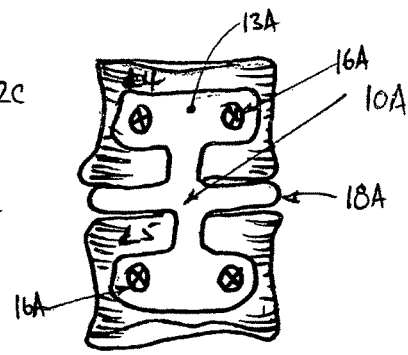

FIG. 2 shows a similar view to FIG. 1 but of a variation on the implant 10 of FIG. 1, namely, a device in the form of an implant 10A, again in a simple form, but in this case the implant is configured for typical use in the lumbar segments of the spine (a subtle variation of the implant 10A is shown in FIG. 12 with the implant 10A shown fixed in position to the anterior face of the vertebrae L4 and L5).

In the implant 10A of FIG. 2, the connecting bracket 12A is wider than the connecting bracket 12 of FIG. 1, due to the increased size (e.g. width) of the lumbar segments of the spine. The implant 10A also has a pad 18A that is integrally formed with the connecting bracket 12A. Further, opposite ends of the connecting bracket 12A are again widened (i.e. for the lumbar segments of the spine) to each define a respective head 13A. Each head 13A comprises two spaced apertures 14A, through each of which a respective surgical fastener 16A (e.g. surgical screw) can be introduced to affix and thereby secure that bead to the anterior face of a given one of the adjacent vertebrae (see e.g. FIG. 12). The two spaced apertures at either end may be required for surgical application in the lumbar and thoracic segments of the spinal column, to provide greater strength, securement and stability.

Figure 13:
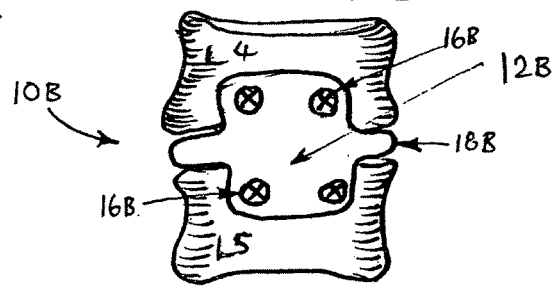

FIGS. 9, 10 and 13 show a variation on the implants of FIGS. 1 and 2. Here the implant 10B is also suitable for use at the lumbar segments of the spine (e.g. to be inserted between L4 and L5 as shown). Again, the connecting bracket 12B is wider than that of the implant of FIG. 1, due to the increased width of the lumbar segments of the spine, however, in this variation that width is preserved throughout the length of the connecting bracket 12B (i.e. so that no "heads" are defined at opposite ends of the connector). Each end of the connecting bracket 12B again comprises two spaced apertures 14B, through each of which a respective surgical fastener 16B (e.g. surgical screw) can be introduced to affix and thereby secure that end to the anterior face of a given one of the adjacent vertebrae (see e.g. FIG. 13).

Figure 11:
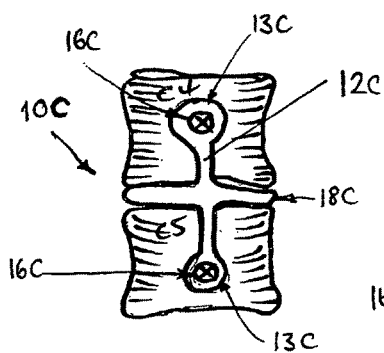
FIGS. 11 to 15 respectively show in-use views of further variations on the implant of the first embodiment.

FIG. 11 shows a further variation on the implant of FIG. 1. Here the implant 10C is suitable for use at the cervical segments of the spine (e.g. to be inserted between C4 and C5 as shown). In this variation, the connecting bracket 12C is narrower than that of the embodiment of FIG. 1, which facilitates increased flexibility, more particularly needed in the cervical region of the spine than might be the case in the lumbar region. In addition, round heads 13C are defined at opposite ends of the connecting bracket 12C. Each round head 13C comprises a single apertures therethrough for receipt of a respective surgical fastener 16C (e.g. surgical screw). The fastener is introduced to affix and thereby secure that head to the anterior face of a given adjacent vertebra.

Figure 14:
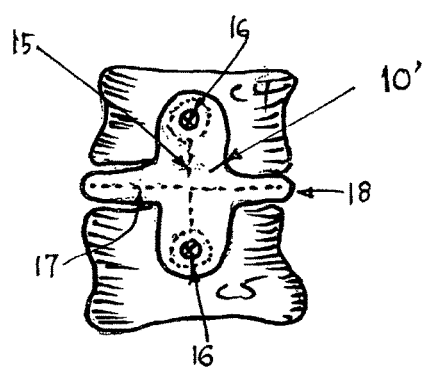

FIG. 14 shows another implant variation 10' on the implant 10 of FIG. 1. In this variation, the implant 10' comprises first and second reinforcing wires 15 and 17 (shown by the dotted lines). These wires are integrally moulded into the implant 10' and pad 18 and give added strength to the implant 10' in use. The reinforcing wire 15 also encircles the fixing apertures 16. Different configurations of the reinforcing wire can be employed to vary the strength, stiffness, resilience, etc of the implant.

Figure 15:
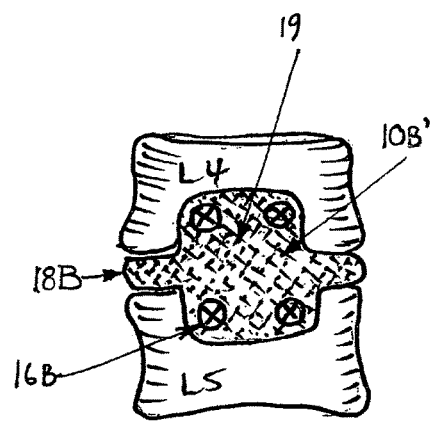

FIG. 15 shows another variation on the implant 10B' of FIGS. 9, 10 & 13. In this variation, the implant 10B' comprises a wire reinforcement mesh 19. This mesh is again integrally moulded into the implant 10B' and pad 18B and gives added strength and resilience to the implant 10B' in use. The reinforcement mesh 19 also encircles the fixing apertures 16B.

The performance and flexibility of the implant and its integrally formed pad of Embodiment 1 and its variations can be varied by varying the gauge, configuration and spacing of the reinforcing wire or wire mesh, as may be needed by a patient post-operatively, in order to satisfy their anticipated life-style needs.

In Embodiment 1 and its variations, the pad 18 is formed (i.e. shaped and configured) for surgical insertion anteriorly in the spine to suit the respective disc space between the adjacent vertebrae. In this regard, the pad 18 can be shaped and configured to approximate the shape of a natural disc at the given spinal location. For example, the approximate size and shape of a typical disc in the cervical segments of the spine is shown in FIG. 69.

The pad 18 can also be varied in thickness depending on which segments of the spinal column are to be treated. For instance, a pad for application in the cervical segments of the adult human spinal column would be typically 2-3 mm in thickness. A pad for application in the thoracic and lumber segments of the adult human spine may be approximately 3-5 mm or 6-8 mm in thickness, respectively.

The pad 18, whether formed of compressible material or rigid material, can be configured for having an adhesive or bone growth promoter introduced therethrough, so as to enable the pad to be (or become) affixed to the adjacent treated vertebrae (this is shown and described hereafter with reference to FIGS. 60 and 61). Such an adhesive or bone growth promoter can 'surface coat' the pad to in turn promote new bone growth between the pad and the adjacent vertebrae.

Embodiment 2—Multiple-Pad Disc Replacement Implant (FIGS. 16-23)

A second device embodiment in accordance with the present disclosure has a more complex form for replacement of two or more degenerated natural discs (this embodiment and its variations are shown in FIGS. 16 to 23).

In this embodiment the device takes the form of an implant 20 that comprises a connector in the form of a flexible connecting bracket 22 for spaning and for interconnecting three adjacent vertebrae (e.g. C3-C5, L3-L5, etc).

Figure 16:
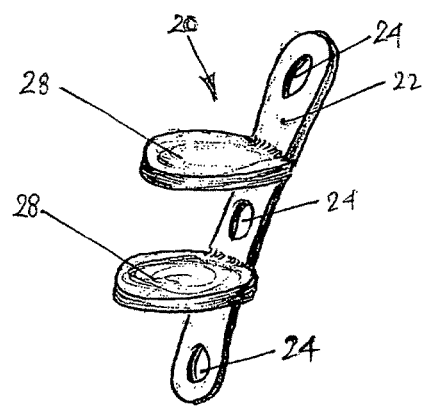
FIG. 16 shows a diagrammatic perspective view of a second embodiment of a device in the form of a two pad implant, typically for use with e.g. the cervical vertebrae.
Figure 17:
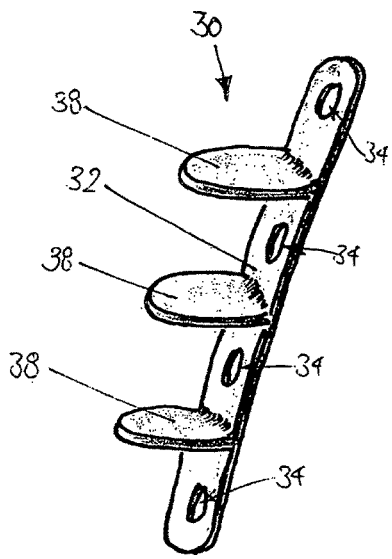
FIG. 17 shows a diagrammatic perspective view of a variation of the second embodiment of a device in the form of a triple pad implant for use typically with e.g. the cervical vertebrae.

More particularly, and as shown in FIG. 16, the connecting bracket 22 is sized to span, and is adapted for interconnecting, three adjacent vertebrae (e.g. the cervical segments of the spine such as the vertebrae C3 to C5 as shown in FIGS. 19-21).

In this regard, three apertures 24 are provided in opposite ends and in the middle of the connecting bracket 22, and through each of which a surgical fastener 26 (e.g. a surgical screw) can be introduced to affix and thereby secure that part of the connecting bracket 22 to the anterior face of a given adjacent vertebra.

The implant 20 also comprises pad elements, each in the form of an integrally formed flexible pad 28 (e.g. moulded at the same time as bracket 22, in the same mould cavity). The integrally formed pad 28 is configured for location with respect to a respective disc space between the at least two adjacent vertebrae (see especially FIG. 20). The pad 28 has a similar disc-like shape and profile and is generally formed from the same material as described above for pad 18.

FIG. 19 shows the two pads 28 ready to be inserted anteriorly into two clear intervertebral spaces between vertebrae C3 and C4, and between C4 and C5. FIG. 20 shows the implant 20 fixed in position between C3 and C4 and C4 and C5. FIG. 21 shows an anterior view of the fixed implant 20 with spinal flexion to the left.

In a variation of this embodiment, an implant 30 comprises an elongate connecting bracket 32 that is sized to span, and that is adapted for interconnecting, four adjacent vertebrae (e.g. the cervical segments of the spine such as the vertebrae C2 to C5). Four apertures 34 are provided in opposite ends of and intermediately in the connecting member 32, and through each of which a surgical fastener (e.g. a surgical screw) can be introduced to affix and thereby secure that part of bracket 32 to the anterior face of a given adjacent vertebra.

The implant 30 also comprises three integrally formed flexible pads 38 (e.g. moulded at the same time as bracket 32, in the same mould cavity), the three pads each having a similar disc-like shape and profile and generally being formed from the same material as described above for pad 18.

Figure 18:
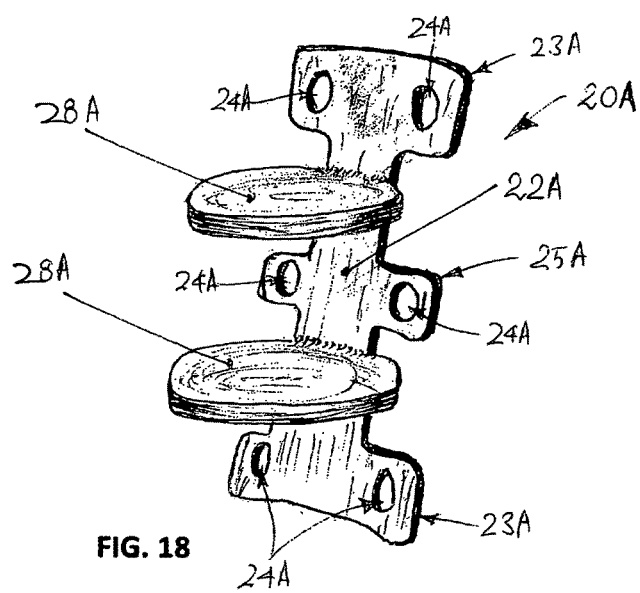
FIG. 18 shows a diagrammatic perspective view of a variation on the implant of the second embodiment of FIG. 16.

FIG. 18 shows a variation of the embodiment FIG. 16, the implant taking a larger flexible format 20A for use typically in the lumbar segments of the spine. As with the embodiment of FIG. 2, the connecting bracket 22A is wider than that of the embodiment of FIGS. 16 & 17, due to the increased size (e.g. width) of the lumbar segments of the spine. Further, opposite ends as well as an intermediate region of the connecting bracket 22A, are again widened (i.e. for the lumbar segments of the spine) to each define a respective head 23A and intermediate lugs 25A. The larger format of implant 20A is also provided with two larger integrally formed pads 28A, each to be respectively positioned and fixed in the lumber or thoracic disc spaces (e.g. between lumbar vertebrae L3 and L4 and between L4 and L5). The pads 28A have a similar disc-like profile and are generally formed from the same material as described above for pad 18A.

As best shown in FIG. 23, each head 23A and each lug 25A comprises two spaced apertures 24A, through each of which a respective surgical fastener 26A (e.g. surgical screw) can be introduced to affix and thereby secure that head to the anterior face of a given adjacent vertebra. The two spaced apertures at each end and intermediately can provide greater strength, securement and stability.

FIG. 22 shows a variation on the implant 20A of FIGS. 18 and 23. In this variation, the implant 20B is shown that also has a larger flexible format for typical use in the lumbar segments of the spine is shown (e.g. at L3 to L5 as shown). The implant 20B differs mainly from the implant 20A in that it comprises an even wider connecting 22B to provide enhanced strength and stability at the lumbar segments of the spine. Otherwise, the implant 20B functions in essentially the same manner as implant 20A.

In Embodiment 2, the implants 20, 30 may be reinforced with at least one relatively rigid, but flexible reinforcing element, which may extend into and form part of the pad to provide added strength and resilience to the implants. For example, the implants 20 and 30 may comprise a moulded polymer (e.g. a bio-compatible polymer) and may be reinforced by a flexible, resilient wire made of inert metal—e.g. of stainless steel, titanium, chrome, etc).

Figure 24:
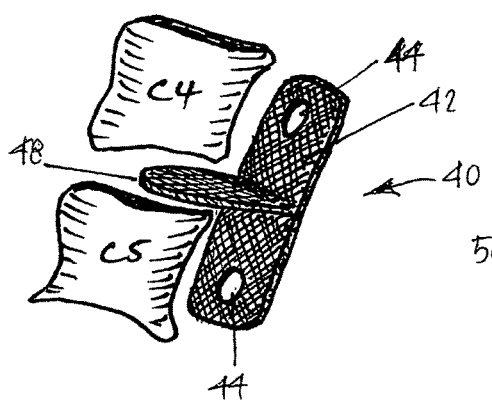
FIG. 24 shows a diagrammatic perspective view of a third embodiment of a device, also in the form of a simple elongate implant, but formed from a flexible polymeric or inert metal mesh material.
Figure 27:
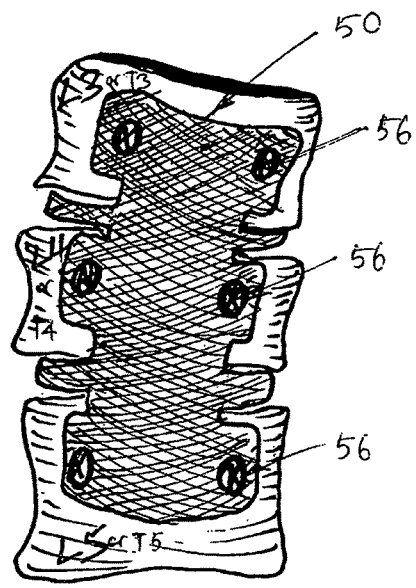

Embodiment 3—Flexible Mesh Implant (FIGS. 24 and 27)

A third device embodiment, in its simplest form, and in accordance with the present disclosure comprises an implant 40 that is formed and configured from a bio-compatible metal or polymer mesh (e.g. woven from metal or polymer wire, or moulded from polymer, etc).

Figure 26:
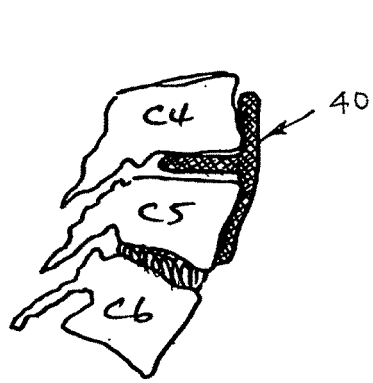
FIGS. 26 and 27 show diagrammatic perspective views of a third embodiment of a device (or a subtle variation of that), also in the form of a simple elongate implant, but formed from a flexible polymeric or inert metal mesh material, showing that device in use.

The implant 40 that is formed from such a mesh is shown in FIGS. 24 and 26, with FIG. 26 showing implant 40 in situ (e.g. extending between vertebrae C4 and C5). The flexible implant 40 is similar in shape to the embodiment of FIG. 1 and, in this regard, comprises an elongate connecting bracket 42, opposing apertures 44, and a pad 48. The pad 48 can be integrally formed (e.g. moulded or fused together, from the same material) with the connector 42.

Figure 25:
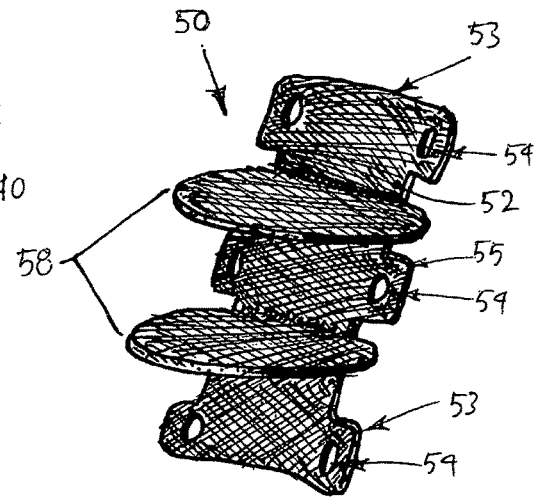
FIG. 25 shows a diagrammatic perspective view of a thid embodiment of a device having twin pads integrally formed with a wider implant formed from a flexible polymeric or inert metal mesh material.

In a variation of this embodiment, shown in FIGS. 25 and 27, an implant 50 that is formed from such a mesh is shown, with FIG. 27 showing the implant 50 in situ (e.g. extending between vertebrae L3 to L5). The flexible implant 50 is similar in shape to the embodiment of FIG. 22 and, in this regard, comprises an elongate connecting bracket 52, having opposing end and intermediate apertures 54, and two pads 58. The pads 58 can again be integrally formed (e.g. moulded or fused together, from the same material) with the connecting bracket 52.

In this third embodiment, within the limits of the flexibility of the mesh, normal movement and mobility of the treated vertebral segments can be restored after the implant of the implants 40, 50. In this regard, when fixed in position to the anterior face of the adjacent vertebrae, the implants 40, 50 can provide stability to the treated segments while also providing flexibility and mobility, depending on the gauge of wire/mesh, as well as the structural configuration of the wire/mesh from which the implant is made.

Embodiment 4—Implant with Insert Pad & Pad Locator (FIGS. 28-31)

A fourth device embodiment in accordance with the present disclosure allows for the replacement or interchanging of pad(s); this embodiment and its variations are shown in FIGS. 28 to 31.

In this embodiment implant 60 comprises a frame 62 that has a connector in the form of an elongate connecting bracket 64. The bracket 64 has an integrally formed pad locator 66 for receipt of an interchangeable insert pad 67 or 67'. The insert pad 67 or 67' may have a shape and/or configuration that approximates or approaches the shape of a natural spinal disc.

The connecting bracket 64 that is configured to span adjacent vertebrae (e.g. C4 and C5; L4 and L5, T4 and T5, etc). The bracket 64 comprises apertures 65 at opposing ends thereof, each for receiving therethrough a respective surgical fastener (e.g. screw). Thus, having inserted the pad locator 66 and pad 67, 67' in the respective intervertebral space, the fasteners affix and secure the implant 60 to the anterior faces of the given adjacent vertebrae.

The pad locator 66 is formed by a lateral (e.g. moulded or affixed) extension of the bracket 64 at its approximate mid-point thereby forming a retaining band to receive and secure in position the insert pad 67 or 67'. The band of pad locator 66 can optionally be reinforced by a wire, filaments, fibres, etc moulded into the band, and integral with reinforcing wire for the bracket 64, to increase band resilience and its ability to retain the insert pad 67 or 67' therein.

The pad locator 66 can be configured to snugly but interchangeably receive the insert pad 67 therein, and the insert pad 67 or 67' can be of a size and shape such it can be press-fit into the pad locator 66, as indicated by FIGS. 28 and 31. This embodiment therefore allows the surgeon to select a pad that is suited to the requirements of a given patient.

The insert pad 67 is provided with (e.g. has moulded thereinto) a perimeter groove 68, as shown in FIG. 29. The groove 68 is configured to receive an inside face of the pad locator 66 once the pad 67 has been press-fitted therein, as shown in FIG. 31. In FIG. 31, upper and lower faces of the pad 67 can sit generally flush with the pad locator 66.

However, interchangeable insert pads 67 can be selected that are configured to vary in size and shape, depending on the segments of the spine that are to be treated and/or to provide for any particular anatomical requirements of the patient.

In this regard, a variation of the insert pad 67 is shown in FIG. 30, as an insert pad 67'. In this variation, the pad 67' is configured to protrude in a pronounced manner above and below the pad locator 66 (i.e. the pad has a defined side wall 69' extending above and below the groove 68', whereby the pad 67' is noticeably thicker than the pad locator 66). Such an insert pad can be employed to allow for preferential pad engagement of the two adjacent vertebrae in use. Such an insert pad can also allow the pad locator 66 to be formed from a stiffer, tougher/stronger material, as it then does not need to provide the natural disc-like simulation.

Other variations of the insert pad can be made to provide different design features and different performance criteria to meet different patient needs and post-operative outcomes, as may be determined by the surgeon in prior consultation with the patient. Such variations encompass the use of different bio-compatible materials from which the insert pads can be formed or otherwise manufactured. For example, in the case of compressible material or non-compressible material, the pads may be formed from e.g. a silicon-based polymer, a polyurethane, etc. Alternatively, the insert pads may be formed from a variety of non-compressible materials which are more functionally rigid (e.g. biocompatible high polyurethane or polyethylene etc).

Variations in insert pads also include different structural features that provide for variations in the resilience of the pads in order to more closely simulate the operational function and performance of the natural disc. In this regard, further variations of the insert pads are shown in FIGS. 62 to 68 and described in more detail under Embodiment 13. For example, the pad may comprise a reservoir (e.g. that is centrally located in the pad). This reservoir may contain a viscous, resilient fluid whereby the fluid-filled reservoir may function like a pulposus of a natural disc and the body of the pad material may function like the annulus of a natural disc.

In this case, the insert pad may be formed from a flexible, resilient, compressible, biocompatible material (e.g. silicon-based polymer) that is configured to simulate a normal intervertebral disc of the spinal column in which the device is to be employed. Alternatively, the insert pad may be formed from a rigid, non-flexible material (e.g. high density polyurethane).

Further, an insert pad that is intended to be positioned within the cervical region may have different performance characteristics (e.g. resilience and/or compressibility) to an insert pad that is intended to be positioned in the thoracic or lumbar segments of the spine.

Alternatively, the insert pad may be formed from a rigid, non-flexible material (e.g. high density polyurethane), of a shape and profile as schematically depicted in FIG. 30.

Embodiment 5—Single or Multi-Strand Wire Implant (FIGS. 32-37)

A fifth device embodiment in accordance with the present disclosure provides a different form of implant 70 which comprises a framework that also allows for the replacement or interchanging of pad(s); this embodiment and its variations are shown in FIGS. 32 to 37.

In this embodiment the implant 70 comprises a wire framework 72 comprising a connecting bracket 74 and an integrally formed locator 76 for receipt of an interchangeable insert pad 77 or 77' (which are closely related in formation and configuration to pads 67, 67', as described above—i.e. pad provided with a peripheral groove to receive therein (e.g. closely or snugly) the single strand or a multi-stranded wire).

This embodiment and its variations generally define an implant having a single wire connecting bracket 74 which might typically be employed in the cervical region of the spinal column rather than the thoracic or lumbar vertebrae, where more robust implants can typically be required. Such robust implants may comprise a multi-stranded framework which may be better adapted to the thoracic or lumbar vertebrae. The multi-stranded framework can provide added strength and rigidity to the implant, as may be required to meet particular patient needs.

In this regard, the framework 72 together with the pad locator 76 can be fabricated from a flexible single or multi-strand inert metal wire (e.g. of surgical steel, stainless steel, titanium, etc), a polymer-coated wire, a composite (e.g. fibre-reinforced) polymer wire, etc. The single strand wire framework 72 is schematically shown in FIGS. 32 to 34, whereas the multi-stranded framework 72' is schematically depicted in FIG. 35.

The single strand wire implant can provide for greater bendability and/or flexibility whereas the multi-stranded metal wire can provide greater stiffness. The wire selected may depend on the severity of the damage to the given intervertebral disc to be replaced and/or the position in the spine. For example greater stiffness may be required in the lumbar vertebral region than might be needed in the cervical region. In either case, the wire is selected to have sufficient resilience to permit rotational, flexion in all directions, and/or pivotal movement of the at least two adjacent vertebrae with respect to each other in use, but so as to maintain acceptable alignment of the vertebrae.

The wire framework 72 or 72' defines an elongate connecting bracket 74, 74' that is configured to span adjacent vertebrae (e.g. C3 and C4 as shown in FIG. 34). The bracket 74 or 74' is fabricated/formed so as to define eyelets 75, 75' at opposing ends thereof, each for receiving therethrough a respective surgical fastener 79 (e.g. screw) to affix and thereby secure the framework 72 to the anterior faces of the given adjacent vertebrae, as shown in FIG. 34. The bracket 74 or 74' can also be reconfigured to define dual eyelets at opposing ends thereof.

The wire framework 72 is further fabricated/formed so as to define a pad locator 76, 76' midway along its length, as shown in FIGS. 32 and 35. The pad locator 76, 76' may comprise a continuation of (i.e. be integral with) the connector 74, or the locator may be fused, welded or otherwise affixed thereto. In any case, the shaping and configuring of the pad locator 76, 76' is such as to define a circular receipt region into which an insert pad 77 or 77' can be press-fitted or otherwise secured, as shown in FIGS. 33 and 35.

The employment of a wire framework can optimally support the implant in use against dislocation, excessive movement or dislodgement from the intervertebral spaces, after surgical insertion of the implants described.

FIGS. 36 and 37 show a variation on the framework, in the form of an implant 80. The implant 80 also comprises a wire framework 82 (i.e. of flexible single or multi-stranded inert metal wire) for receipt of two interchangeable insert pads 87 or 87' (akin to pads 67, 67'). However, this variation is reconfigured to define an implant for spanning three cervical vertebrae, and for replacing two diseased discs (see FIG. 37).

In this regard, the wire framework 82 is further fabricated or formed to define a connecting bracket 84 with increased elongation (i.e. to span three or more vertebrae). In addition, two (or more) intermediate pad locators 86A and 86B are provided along the length of connecting bracket 84, as shown in FIGS. 36 and 37. Again, the pad locators 86A and 86B may comprise a continuation of (i.e. be integral with) the connecting bracket 84, or the locator may be fused, welded or otherwise affixed thereto.

Alternatively, the pad locators 86A and 86B can be connected to the bracket 84 such that there can be rotational movement at the point where the pad locators connect to bracket 84.

In any case, the pad locators 86A and 86B define a receipt region into which an insert pad 87 or 87' can be press-fitted or otherwise secured, as shown in FIGS. 36 & 37.

The connecting bracket 84 is fabricated/formed so as to define eyelets 85 at opposing ends thereof, as well as an intermediate eyelet 85A, each for receiving therethrough a respective surgical fastener 89 (e.g. screw) to affix and thereby secure the framework 82 to the anterior faces of the three respective and adjacent vertebrae, as shown in FIG. 37.

The implant variations that comprise multiple pad locators may be varied in shape and size to meet particular clinical needs of the patient, as schematically shown in FIG. 36, where pad locator 86A is slightly larger than pad locator 86B, though both are still integrally formed together with or secured to connecting bracket 84.

Because of the integrated structural integrity of the implant 70, 70', 80 in this embodiment, support and stability is provided to the segments treated whilst mobility and flexibility are preserved, within the normal range of movement in the segments surgically treated.

Embodiment 6—Single or Multi-Strand Wire Frame Implant (FIGS. 38-43)

A sixth device embodiment in accordance with the present disclosure provides a wire framework that is similar to Embodiment 5 and which also allows for the replacement or interchanging of pad(s); this embodiment and its variations are shown in FIGS. 38 to 43.

In this embodiment an implant 90 comprises a single, continuous wire strand frame 92 for receipt of an interchangeable compressible insert pad 97 or more rigid insert pad 97' (both of which are closely related in formation and configuration to pads 67, 67', as described above—i.e. the pads are provided with a peripheral groove to receive therein (e.g. closely or snugly) the single, continuous wire strand of frame 92).

Again, the variations of this embodiment shown in FIGS. 38 to 41 generally define an implant which might typically be employed in the cervical region of the spinal column rather than the thoracic or lumbar vertebrae, where more robust implants can typically be required. However, when the single wire strand of frame 92 is substituted with a multi-stranded wire, the implant may be better adapted to the thoracic or lumbar vertebrae as depicted in FIGS. 42 and 43, whereby the multi-stranded wire frame can provide added strength and rigidity to the implant, as may be required to meet particular patient needs.

The frame 92 can be fabricated from a single or multi-strand inert metal wire (e.g. of surgical steel, stainless steel, titanium, etc), a polymer-coated wire, a composite (e.g. fibre-reinforced) polymer wire, etc.

The frame 92 defines, in effect, an elongate connecting bracket comprising two parts, an upper part 94U and a lower part 94L. The upper connector part 94U is formed so as to define an upper eyelet 95U that is configured for receiving therethrough a respective surgical fastener 99 (e.g. screw) to affix and thereby secure the upper connector part 94U to the anterior face of the given adjacent vertebrae, as shown in FIG. 39. Likewise, the lower connecting bracket part 94L is formed so as to define a lower eyelet 95L that is also configured for receiving therethrough a respective surgical fastener 99 (e.g. screw) to affix and thereby secure the lower connector part 94L to the anterior face of the given adjacent (underlying) vertebrae. Thus, the implant 90 with its elongate connecting bracket, can span adjacent vertebrae (e.g. C3 and C4) or span three or more vertebrae (as necessary) depending on the clinical needs of the patient.

The frame 92 is further formed so as to define a pad locator 96 midway along its length, as shown in FIG. 38. The pad locator 96 is a continuation of (i.e. integral with so as to connect) the upper and lower bracket parts 94U and 94L of the frame 92. The shaping and configuring of the pad locator 96 is such as to define a receipt region into which the insert pad 97 or 97' can be press-fitted or otherwise secured.

A variation on the implant 90 labelled implant 100, is shown in FIGS. 40 and 41. Implant 100 comprises two (or more) pad locators 106' and 106", each of which is a respective continuation of (i.e. integral with) the upper connector part 104U and the lower connector part 104L. Each pad locator 106' and 106" is shaped and configured to define a receipt region into which the insert pads 107' and 107" can be press-fitted or otherwise secured.

However, the implant 100 also comprises an intermediate connector part 104I that is a continuation of (i.e. integral with) the pad locators 106' and 106".

Also, the upper connector part 104U is formed to define an upper eyelet 105U for a surgical fastener 109, the lower connector part 104L is formed to define a lower eyelet 105L for another surgical fastener 109, and the intermediate connector part 104I is formed to define an intermediate eyelet 105I for yet another surgical fastener 99. These three eyelets enable the implant 100 to be affixed and thereby secured to the anterior faces of three respective and adjacent vertebrae, as shown in FIG. 41, so that the implant 100 extends between the adjacent vertebrae (e.g. C4 to C6 as shown).

A variation on the implant 100 is shown as implant 110 in FIGS. 42 and 43. The implant 110 is much like the implant 100, other than in respect of the upper eyelet 105U and the lower eyelet 105L. FIG. 43 shows the implant 110 in use, with prosthetic pads 117' and 117" accommodating spinal flexion to the left.

In this variation, the implant 110 comprises two upper eyelets 115U' and 115U", each for a respective surgical fastener 119, and each connected and defined by an extension member 114E' located at the end of the upper connector part 114U (e.g. by being affixed, fused or integrally formed therewith). Similarly, the implant 110 comprises two lower eyelets 115L' and 115L", each for a respective surgical fastener 119, and each connected by an extension member 114E" located at the end of the lower connector part 114L (e.g. by being affixed, fused or integrally formed therewith).

These additional eyelets and extension members enable the implant 110 to be affixed and better secured to the anterior faces of respective and adjacent larger (e.g. lumbar or thoracic) vertebrae, as shown in FIGS. 42 and 43, so that the implant 110 is able to be deployed at and can extend between such vertebrae (e.g. L3 to L5 as shown). In this regard, the implant 110 now has five screw fixing points.

Again, the flexibility of the implants 90, 100, 110 can be varied by varying the gauge and tensile strength of the wire. This sixth embodiment also provides stability and flexibility, post-operatively, of the segments treated, again within the normal range of movement. Because the pad locators are integrally formed and configured with the implants 90, 100, 110, when they are fixed in position, the implants are optimally designed against dislocation, excessive movement or dislodgement, while providing flexibility in the vertebral segments treated, within the normal range of movement.

In another variation on the use of the implants 90, 100, 110, and to provide some tolerance for excessive movement post-operatively, the eyelets can be lined with a washer-like bush 91B (FIG. 39), composed of a tough resilient material (e.g. a high density, biocompatible polymer such as polyurethane). This allows for the use of smaller diameter fixing screws, such that there is some tolerance for differential movement between the screw shafts at the bush-lined eyelets. This can allow for extreme flexion and rotation of the spine and/or post-operative realignment or minor settlement of the treated segments of the spinal column.

Embodiment 7—Pad Locator Adjustment (FIGS. 44-48)

A seventh device embodiment in accordance with the present disclosure provides another implant that allows for the longitudinal adjustment of pad(s)/locator(s); this embodiment and its variations are shown in FIGS. 44 to 48.

In a first form of this embodiment an implant 120, shown in FIGS. 44 and 45, comprises an elongate connecting bracket 121 that is formed to have three respective upper, intermediate and lower eyelets 122U, 122I and 122L. Each eyelet is configured for receiving therethrough a respective surgical fastener 129 (e.g. a screw) to affix and thereby secure the connecting bracket 121 to the anterior face of three respective and adjacent vertebrae, as shown in FIG. 45 (e.g. C3 to C5).

The implant 120 also comprises two longitudinally adjustable pads/locators 123 and 124, with the up-and-down adjustment along the bracket 121 being illustrated schematically by the double-headed arrows in FIG. 44. The longitudinal adjustment of the pads/locators can accommodate variances in intervertebral spaces which may occur during surgical procedures and/or for different patients (e.g. due to vertebral compression).

To facilitate the longitudinal adjustment, a given pad can be formed with, or can be fabricated to have, an extension 125. The extension 125 can be affixed to the pad to extend laterally therefrom and thereby allow the pad to connect to and slide along the connecting bracket 121. Alternatively, the extension 125 can form an integral part of a pad locator, the latter of which separately receives and locates an insert pad therein (e.g. an interchangeable compressible or more rigid insert pad, both of which can be somewhat related in form to the pads 67, 67', as described above).

In implant 120, each extension 125 comprises a ring of material (e.g. of inert metal or composite polymer, etc) that is sized to slide along the connecting bracket 121. In this regard, an upper extension 125U locates and is able to slide on the connecting bracket 121 between the upper and intermediate eyelets 122U and 122I, whereas a lower extension 125L locates and is able to slide on the connecting bracket 121 between the intermediate and lower eyelets 122I and 122L.

By forming each extension 125 of a ring of material, each pad/locator 123, 124 can also rotate on the connecting bracket 121, providing a surgeon with a further degree of freedom of adjustment when locating each pad/locator 123, 124 between adjacent vertebrae.

The materials of the connecting bracket 121, the pads/locators 123, 124 and the extensions 125U and 125L can generally be the same as for previous embodiments, and hence will not be redescribed.

The implant 120 might typically be employed in the cervical region of the spinal column rather than the thoracic or lumbar vertebrae, where more robust devices can typically be required. However, it may be adapted to the thoracic or lumbar vertebrae.

In use, the implant 120 can allow for spinal flexion to the right and left and in all directions, for example, depending on the flexibility and configuration of the material from which implant 120 is made. In use, the pads can be cemented to the upper and lower surfaces of the adjacent vertebrae to ensure against unwanted movement or dislocation of the pads.

A variation implant 130 is shown in FIG. 46. Here, the elongate circular cross-sectioned connecting bracket 121 is replaced with an elongate connector 131 that is formed from a square section of inert metal or other plastic-coated, or polymer composite material, each of which is bio-compatible.

In implant 130, each extension 135 of each pad/locator 133, 134 comprises a flexible or rigid square-sectioned ring of material 136 (e.g. of inert metal or composite polymer, etc) that is again sized to snugly slide along the connector 131. However, because of the matching square sections, each pad/locator 133, 134 is unable to rotate on the connecting bracket 131, thereby removing from the implant 130 a degree of freedom of adjustment, such as when locating each pad/locator 133, 134 between adjacent vertebrae. With this "anti-rotation" constraint, there may then be no requirement for the pads to be cemented to upper and lower surfaces of adjacent vertebrae in use.

Another implant variation is shown in FIG. 47 in the form of an implant 140 that has extra degrees of freedom, as described in further detail below. Here, the connecting bracket 121 is replaced with an elongate connecting bracket 141 of generally C-shaped channel. Again, the C-shaped channel 141 can be formed from a section of inert metal, or a plastic-coated metal, or polymer composite material, or biocompatible plastic, or a semi-rigid material (e.g. polyurethane etc).

Further, the C-shaped channel 141 comprises opposing flanges 142' and 142" that extend along either side of the channel opening and for its length, which flanges have a series of fixing holes 146 formed along their lengths. Each fixing hole 146 can receive therethrough e.g. a small surgical fastener (such as a surgical screw) to affix and thereby secure the flanges 142' and 142" to the anterior faces of respective and adjacent vertebrae.

In implant 140, a distal end of each extension 145 of each pad/locator 143, 144 comprises a ball 147 (e.g. of a hard-wearing inert metal or composite polymer, or plastic, or polyurethane etc), that is again sized to snugly slide along and inside the C-shaped channel 141 (i.e. whereby each extension 145 extends through the C-shaped channel opening 148.

In implant 140, each pad/locator 143, 144 is able to rotate around a transverse axis that extends through the extension 145 and pad/locator. Each pad/locator 143, 144 is further able to be pivoted/tilted up and down with respect to connecting bracket 141. Further, each pad/locator 143, 144 is able to be pivoted side-to-side in connecting bracket 141, however, to a more limited degree, thereby limiting this degree of freedom. Thus, the configuration of implant 140 provides for a range of adjustments when locating each pad/locator 143, 144 between adjacent vertebrae. Again, there may or may not be a requirement for the pads to be cemented to upper and lower surfaces of adjacent vertebrae in use.

In use, implant 140 allows for multiple rotations/pivots of each pad/locator 143, 144 with respect to the channel 141 to accommodate a range of spinal flexion and movement, which can be further adjusted depending on the flexibility and configuration of the material from which implant 140 is made.

A further implant variation is shown in FIG. 48 in the form of an implant 150. Here, the C-shaped channel 141 is replaced with an almost fully closed rectangular hollow section 151, save for the opening 158 through which extends the extension 155 of each pad/locator 153, 154. The opening 158 is defined by opposing angle flanges 152' and 152" that extend along either side of the opening and for its length. The angle flanges 152' and 152" have a series of larger fixing holes 156 formed along their lengths. Each fixing hole 156 can receive therethrough a larger surgical fastener (e.g. screw) to affix and thereby secure the flanges to the anterior faces of respective and adjacent vertebrae.

Also in implant 150, the ball 147 is replaced with a rectangular block 157 (e.g. of hard-wearing inert metal or composite polymer, etc) that is again sized to snugly slide along and inside the rectangular hollow section 151 (i.e. whereby each extension 155 extends through the opening 158 as shown).

This configuration of implant 150 (i.e. block 157 snugly received in corresponding section 151) is such that each pad/locator 153, 154 is unable to rotate at the hollow section 151, thereby again eliminating this degree of freedom of adjustment when locating each pad/locator 143, 144 between adjacent vertebrae. Again, for this reason, there may be no requirement for the pads to be cemented to upper and lower surfaces of adjacent vertebrae in use.

In use, implant 150 allows for multiple rotations/pivots of each pad/locator 153, 154 with respect to the section 151 to accommodate a range of spinal flexion and movement, which can be further adjusted depending on the flexibility and configuration of the material from which implant 150 is made.

Also, this more robust configuring of implant 150 can make it suitable for use with and at thoracic and lumbar vertebrae.

In Embodiment 7 the relative location of each pad/locator can be adjusted in situ, such as during a surgical procedure, to accommodate differential spacings of a given patient.

Embodiment 8—Key-in Connection of Pad Locator to Bracket (FIGS. 49 and 50)

An eighth device embodiment in accordance with the present disclosure, in this case implant 160, allows for the keying-in and longitudinal adjustment of pad(s)/locator(s); this embodiment is shown in FIGS. 49 and 50.

The implant 160 comprises a connector in the form of a connecting band 161 that is again formed to have three respective upper, intermediate and lower eyelets 162U, 162I and 162L. Again, each eyelet is configured for receiving therethrough a respective surgical fastener 169 (e.g. a screw) to affix and thereby secure the connector 161 to the anterior face of three respective and adjacent vertebrae, as shown in FIG. 50 (e.g. thoracic vertebrae T3 to T5).

The implant 160 also comprises two longitudinally adjustable pads/locators 163 and 164, but which have a more limited range of up-and-down adjustment in the bracket. In this regard, the degree of longitudinal adjustment of the pads/locators is delimited by the length of slots 168 that are formed in the connecting band 161, as explained in further detail below. However, the slot length is still sufficient to accommodate most of the variances that can occur in intervertebral spaces during surgical procedures and/or for different patients.

It can also be seen that, depending on the length and span of connector band 161, an intermediate slot 168I can define the intermediate eyelet 162I (i.e. they may be used for dual purposes).

To facilitate the longitudinal adjustment, a given pad can be formed with, or can be fabricated to have, an extension 165 (e.g. of inert metal or composite polymer, etc). The extension 165 can be affixed to the pad to extend laterally therefrom and thereby allow the pad to be connected to the connecting band 161. Alternatively, the extension 165 can form an integral part of a pad locator, the latter of which separately receives and locates an insert pad therein (e.g. an interchangeable compressible or more rigid insert pad, both of which can be somewhat related in form to the pads 67, 67', as described above).

In implant 160, a distal end of each extension 165 is provided with a T-type head 167 that is sized to be inserted into a given slot 168 of the connecting band 161 when a given pad/locator 163 or 164 is rotated transversely by 90° (i.e. in a "key-in" type connection). Once inserted, the given pad/locator 163 or 164 is rotated transversely by 90°, to thereby connect the pad/locator to the connecting band 161.

Once so connected, each pad/locator 163, 164 is able to rotate around a transverse axis that extends through the extension 165 and pad/locator. Each pad/locator 163, 164 is further able to be pivoted/tilted up and down with respect to the connecting band 161. Further, each pad/locator 163, 164 is able to be pivoted side-to-side at the connecting band 161, however, to a more limited degree, thereby limiting this degree of freedom. Thus, the configuration of implant 160 provides for a range of adjustments when locating each pad/locator 163, 164 between adjacent vertebrae. Again, there may or may not be a requirement for the pads to be cemented to upper and lower surfaces of adjacent vertebrae in use.

In use, implant 160 allows for multiple rotations/pivots of each pad/locator 163, 164 with respect to the connecting band 161 to accommodate a range of spinal flexion and movements, which can be further adjusted depending on the flexibility and configuration of the material from which implant 160 is made.

The materials of the connecting band 161, the pads/locators 163, 164 and the extension 165 and T-type head 167 can generally be the same as for previous embodiments, and hence will not be redescribed.

The implant 160 can be employed in the thoracic, lumbar or cervical regions of the spinal column, by varying the size of the implant and its component parts and by carefully selecting the choice of materials from which it is formed.

The connecting band 161 can be shortened to span two vertebrae, or elongated to span more than three vertebrae, with closely spaced slots 168 along its length into which corresponding T-type heads 167 of the pads/locators can be inserted and then turned 90°, thereby securing each pad/locator to the bracket so that they can be aligned to the respective intervertebral spaces preparatory to insertion. The relative location of each pad/locator can be adjusted in situ, such as during a surgical procedure, to accommodate differential intervertebral spaces of a given patient.

For maximum flexibility of adjustment, the connecting band 161 can be modified to have a continuous slot along most of its length. This slot may be provided with retaining lips along its sides to receive other engaging element types (e.g. that are ball-shaped or rectangular-shaped, or quick-fit couplings, etc). Once such engaging elements are inserted into the slot of the connecting band, the pad locators become secured thereto but can still slide along the slot to be positioned for insertion in a respective intervertebral space.

Embodiment 9—Telescoping Bracket for Aligning Pad Locator/s to Intervertebral Spaces (FIGS. 51-55)

A ninth device embodiment in accordance with the present disclosure provides an implant 170 that is length adjustable; this embodiment and its variations are shown in FIGS. 51 to 54.

In the embodiment of FIGS. 51 and 52, the implant 170 comprises an elongate, length adjustable (e.g. telescopic) connecting bracket 171 that comprises an upper eyelet 172U located at a distal upper end of a connector telescoping part 176, and a lower eyelet 172L located at a distal lower end of a connector tubular part 177 (the latter slidably receiving the telescoping part 176 therewithin).

As shown in FIG. 52, the parts 176 and 177 are each affixed to the anterior faces of respective adjacent vertebrae via a respective surgical fastener (e.g. screw) 179 inserted through their eyelets 172U and 172L. Both parts 176 and 177 are of a flexible bio-compatible metal or plastic, e.g. polyurethane etc, as illustrated by the bending in FIG. 52.

The implant 170 also comprises one (FIG. 51) or two (FIG. 52) longitudinally adjustable pads/locators 173 and 174 (i.e. that are akin to the pad/locators 123, 124 described above for embodiment 7).

In this regard, each extension 175 of each pad/locator 173, 174 comprises a ring of material (e.g. of inert metal or composite polymer, etc) that is sized to slide along both parts 176 and 177 of the connecting bracket 171, between the upper eyelet 122U and the lower eyelet 122L, with the up-and-down adjustment being illustrated schematically by the double-headed arrow in FIG. 51. Each pad/locator 173, 174 can also rotate on both parts 176 and 177 of the connecting bracket 171, providing a surgeon with a further degree of freedom of adjustment when locating each pad/locator 173 between adjacent vertebrae.

The lengthening/contracting (e.g. due to telescoping) of the connecting bracket 171, and the up-and-down adjustment of each pad/locator 173, 174, can allow the implant 170 to span to a next (upper or lower) vertebra, and can also accommodate variances in intervertebral spaces which may occur during surgical procedures and/or for different patients. In this regard, the one bracket may be able to telescope to span two, three or even more vertebrae, and may have pads/locators added thereto accordingly.

The materials of the connecting bracket 171, the pads/locators 173, 174 and the extensions 175 can generally be the same as for previous embodiments, and hence will not be redescribed.

FIGS. 53 and 55 show a variation of the embodiment of FIGS. 51 and 52, this variation having a more robust configuration (e.g. for lumbar or thoracic use). In this variation the implant 180 comprises a length-adjustable, telescopic band-like connecting bracket 181. The connecting bracket 181 comprises an upper eyelet 182U located at a distal upper end of a connector telescoping band 186, and a lower eyelet 182L located at a distal lower end of a hollow band part 187 (the latter slidably receiving the telescoping band 186 therewithin).

Again, the parts 186 and 187 can each be affixed to the anterior faces of respective adjacent vertebrae via respective surgical fasteners 189 (FIG. 55) inserted through their eyelets 182U and 182L. Both parts 186 and 187 can be of a flexible or a relatively stiffer bio-compatible metal or plastic, depending on the patient's requirements.

One (or more than one) pad/locator 183 is affixed via an extension mount 185 to the hollow band part 187. That (or another) pad/locator can alternatively (or also) be affixed via the extension mount 185 to the telescoping band 186. Thus, to move a given pad/locator up-and-down, the parts 186 and 187 are extended/or contracted telescopically. This adjustment is illustrated schematically by the double-headed arrow in FIG. 53.

FIG. 54 shows a different implant embodiment 190 to those shown in FIGS. 51 to 53 and 55. In the implant 190 the connector bracket 191 is not length-adjustable, nor telescopic.

The bracket 191 does, however, comprise an upper eyelet 192U located at its upper end, and a lower eyelet 192L located at its lower end. Again, the ends of the connector band 191 can be affixed to the anterior faces of respective adjacent vertebrae via respective surgical fasteners inserted through the eyelets 192U and 192L. Also, the bracket 191 can be of a flexible or a relatively stiffer bio-compatible metal or plastic, depending on the patient's requirements.

In this variation the mounting of each of the pads/locators 193, 194 to the connecting bracket has a more robust configuration (e.g. for lumbar or thoracic use, or to eliminate the use of pad-to-vertebra cement). More specifically, each pad/locator 193, 194 comprises an extension sleeve 195 that slidably mounts on, and receives for sliding therewithin, the connector band 191. Thus, each pad/locator is able to be securely slid up-and-down on the connector band 191, with this adjustment being illustrated schematically by the double-headed arrows in FIG. 54.

The bracket variations of embodiment 9 each allow fine adjustment of the pad/locator, particularly where there is porosity in parts of diseased or otherwise damaged, crushed or abnormal vertebrae. The bracket variations of embodiment 9 provide for such fine adjustments.

Embodiment 10—Pivoting of the Pad Locator to the Bracket (FIGS. 56 and 57)

A tenth device embodiment in accordance with the present disclosure provides an implant that combines pivoting and flexing; this embodiment is shown in FIGS. 56 and 57.

In this embodiment an implant 200 comprises an elongate and flexible connecting bracket 201 of a biocompatible polymer or polymer composite. The shape and configuration of connecting bracket 201 can be varied depending on the segments of the spinal column to be treated and/or the clinical needs of the patient. This embodiment allows for full flexibility (lateral movement, flexion forward and backwards) of the treated vertebrae, within the normal range of spinal movement, as schematically shown in FIG. 57.

The connecting bracket 201 comprises an upper eyelet 202U located at its upper end, and a lower eyelet 202L located at its lower end. These ends are each affixed to the anterior faces of respective adjacent vertebrae via a respective surgical fastener (e.g. screw) 209 inserted through their eyelets 202U and 202L.

The implant 200 also comprises a pivotally adjustable pad/locator 203 that is pivotally mounted to the connecting bracket 201 via a pivot pin 205 (e.g. of inert metal or composite polymer, etc). This configuration allows for up-and-down and side-to-side pivotal movement/adjustment, providing a surgeon with degrees of freedom of adjustment when locating each pad/locator 203 between adjacent vertebrae, as well as adjustment during use of the implant 200.

The connecting bracket 201 can be lengthened to span two, three or even more vertebrae, and may have further pads/locators pivotally mounted thereto accordingly.

The materials of the connecting bracket 201, the pad/locator 203 and the pivot pin 205 can generally be the same as for previous embodiments, and hence will not be redescribed.

Embodiment 11—Dovetail Device (FIGS. 58 and 59)

An eleventh device embodiment in accordance with the present disclosure also provides an implant that combines pivoting and flexing, much like the tenth embodiment; this embodiment is shown in FIGS. 58 and 59.

However, the implant 210 of this embodiment has a "dovetail" configuration 216 at one end to enable close positioning of a like implant 210, as shown in FIGS. 58 and 59. This "dovetailing" or "inter-meshing" of adjacent ends of implants effectively provides for continuous support along those vertebrae to which the implants are affixed. And yet, each implant 210 can still function independently of each other implant. This, together with the pivotal mount 215 of the pad locator 213, results in an implant that provides optimum flexibility and mobility, while providing strength and structural stability to the vertebral segments treated.

Again, the implant 210 comprises an elongate and flexible connecting bracket 211 of a biocompatible polymer or polymer composite, which can be varied depending on the segments of the spinal column to be treated and/or the clinical needs of the patient.

The connecting bracket 211 comprises an upper eyelet 212U located at its upper end, but is bifurcated at its lower end to thereby define the dovetail configuration 216 at that end. In addition, two lower eyelets 212L' and 212L" are able to be provided located at the lower end. The upper and lower ends are in turn affixed to the anterior faces of respective adjacent vertebrae via respective surgical fasteners (e.g. screws) 219 inserted through their eyelets 212U, 212L', 212L".

Again, each implant 210 also comprises a pivotally adjustable pad/locator 213 that is pivotally mounted to the connecting bracket 211 via a pivot pin 215 (e.g. of inert metal or composite polymer, etc) to allow for up-and-down and side-to-side pivotal movement/adjustment, thereby providing degrees of freedom to the surgeon, as well as during use of the implant 210.

Each connecting bracket 211 can be lengthened to span two, three or even more vertebrae, and may have further pads/locators pivotally mounted thereto accordingly.

The materials of the each implant 210 can generally be the same as for previous embodiments, and hence will not be redescribed.

Embodiment 12—Introduction of Adhesive Cement or Bone Promoter (FIGS. 60 and 61)

A twelfth device embodiment in accordance with the present disclosure provides an implant that is flexible and that is much like the implant of embodiment 1 in configuration; this embodiment is shown in FIGS. 60 and 61.

However, the implant 220 of this embodiment comprises a transverse passage 225 that extends from the outside face of the connecting bracket 221 and transversely part-way through the pad/locator 223. The transverse passage 225 allows for the pad/locator 223 to be cemented to upper and lower surfaces of adjacent vertebra, as schematically shown in FIG. 61. FIG. 61 shows one likely pattern of distribution of adhesive cement C (and/or bone growth promoter) after introduction, showing filled irregularities of the upper and lower surfaces of the vertebrae.

The transverse passage 225 terminates at an approximate centre within the pad/locator 223, where it intersects with a vertical passage 226 that extends vertically through the pad/locator 223, as best shown in FIG. 60. Passage 226 is open at both ends with such "cement exits" being located at the approximate centre of the upper and lower surfaces of the pad/locator 223. These interconnecting passages 225 and 226 provide for the introduction of a suitable adhesive cement or bone promoter, such as by a syringe S or the like. In this regard, the transverse passage 225 is configured such that a needle N of the syringe S is able to be inserted therein, and the syringe contents injected to flow through the interconnecting passages 225 and 226 to exit at the centres of the upper and lower surfaces of the pad/locator 223, adjacent to the upper and lower surfaces of adjacent vertebra.

Once introduced the cement is able to fill irregularities in the upper and lower surfaces of adjacent vertebrae and thereby permanently fix the pad/locator 223 to the adjacent vertebrae and thereby fuse the adjacent vertebrae together. The bone growth promoter may "surface coat" the pad/locator 223 to in turn promote new bone growth between the pad/locator 223 and adjacent vertebrae. A combined cement/promoter formulation may also be introduced.

This option can be carefully performed by the attending surgeon to ensure that the introduced adhesive or bone growth promoter is kept within the disc space and not allowed to flow to soft tissue.

In cases where the pad/locator comprises a flexible and compressible material, mobility of the segments cemented together will then depend on the flexibility of the material that forms the pad/locator. In cases where the pad/locator comprises a rigid, non-flexible material the adjacent vertebrae effectively become fused together by the cement and little to no movement between the adjacent vertebrae occurs. Fusing adjacent vertebrae in this way may be a preferred outcome in particular circumstances, as may be determined by the surgeon in consultation with the patient.

As with embodiment 1, each connecting bracket 221 can be lengthened to span two, three or even more vertebrae, and may comprise further pads/locators accordingly. The materials of the each implant 220 can generally be the same as for embodiment 1, and hence will not be redescribed.

Figure 62:
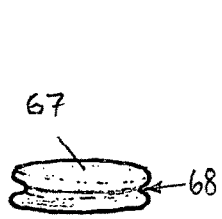
Figure 63:
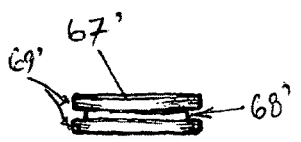
Figure 64:
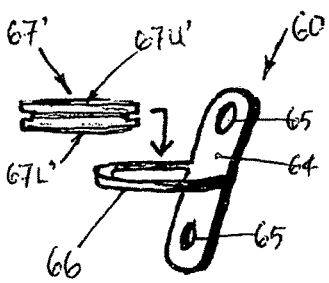

Embodiment 13—Insert Pad Variations (FIGS. 62 to 68)

in the thirteenth embodiment in accordance with the present disclosure, different insert pad options are outlined. The insert pads shown in FIGS. 62, 63 and 64 are the same as or similar to those shown and described for embodiments 4 to 6. The insert pads shown in FIGS. 68A, B and C are the same as or similar to those shown and described for embodiments 4 to 6, but are of increasing size respectively for use with cervical, thoracic and vertebrae.

In this regard, the insert pad embodiment 67 shown in FIG. 62 comprises a compressible material and has a peripheral groove 68 (for a pad locator). The insert pad embodiment 67' shown in FIG. 63 comprises a relatively incompressible (rigid, stiff) material and has a peripheral groove 68' and a defined side wall 69' extending above and below the groove 68' (for a pad locator). The insert pad embodiment 67' shown in FIG. 64 for insertion into a pad locator 66 of implant 60 may additionally have a convex profile at its upper 67U' and lower 67L' vertebrae-facing surfaces, whereby such surfaces preferentially engage the respective upper and lower vertebrae. The choice of a compressible or incompressible pad will be made by the surgeon, in consultation with, and taking account of, the individual patient's requirements.

Figure 65:
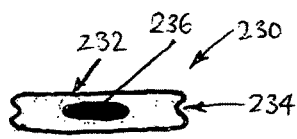

The insert pad embodiment 230 shown in cross-section in FIG. 65 comprises a body 232 of compressible or relatively incompressible material which again has a peripheral groove 234 (for a pad locator). A pulposus-simulating core 236 (e.g. of a denser material, of a closed-cell polymer, a liquid-filled cell or sack, or another material that simulates a natural pulposus) is formed (e.g. 3D printed, moulded, etc) within the body 232. The resultant insert pad 230 is better able to simulate the characteristics of a natural disc.

Figure 66:
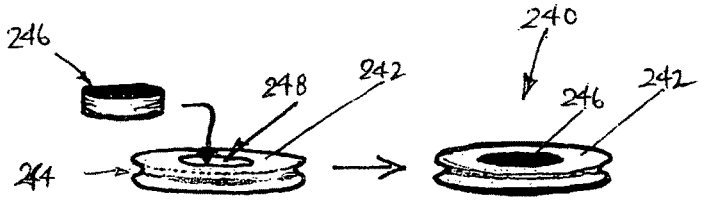
Figure 67:
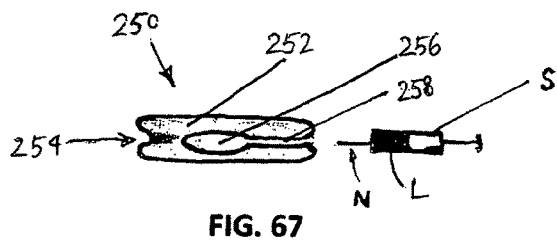

The insert pad embodiment 240 shown in FIG. 66 comprises a tyre-like shaped outer rim 242 of compressible or relatively incompressible material which is configured to simulate the annulus of a natural disc, and that again has a peripheral groove 244 (for a pad locator). An additional pulposus-simulating cylindrical insert 246 (e.g. of a closed-cell polymer, a liquid-filled cell, or other material that simulates a natural pulposus) is affixed within the hollow 248 of annulus 242 (i.e. to extend right through the insert pad 240). Again, the resultant insert pad 240 (right-handside of FIG. 66) is better able to simulate the characteristics of a natural biological disc.

The insert pad embodiment 250 shown in FIG. 68 comprises a pad similar to the pads 67 and 67' that are schematically depicted in FIGS. 62 and 63, but having a centrally located hollow body 252 of compressible resilient or semi-compressible material which again has a peripheral groove 254 (for a pad locator). The hollow sac region 256 is able to receive therein, via a transverse passage 258, and e.g. by injection from a syringe S and needle N, a pulposus-simulating liquid L (e.g. a settable/curable or non-setting liquid or polymer, or another material that simulates a natural pulposus). Once injected, or once the material L cures, the transverse passage 258 is (or becomes) closed up (e.g. is blocked or plugged). The transverse passage 258 may also be filled when the insert pad is in situ in the intervertebral space. Yet again, the resultant insert pad 250 is better able to simulate the characteristics of a natural disc.

The various insert pads as described for embodiment 13 can each be used with variations of implants having pad locators as set forth above in any of the aforementioned embodiments, and suitable bio-compatible polymers or composites can be employed in their fabrication, and so as to simulate the function and performance of a natural intervertebral disc of the spinal column.

Further, the insert pads intended to be positioned within the cervical region of the spinal column may have different performance characteristics (e.g. resilience and/or compressibility) compared to insert pads that are intended to be positioned within the thoracic or lumbar regions of the spinal column and, depending on the needs and post-operative expectations of the patient, as may be determined by the surgeon. In addition, the insert pads may be of different sizes both in diameter and thickness, as schematically shown in FIG. 68, depending on whether the segments to be treated are in the cervical (A), thoracic (B) or lumbar (C) vertebral segments of the spine.

The various intervertebral implant embodiments disclosed herein can be manufactured via a variety of methods including additive techniques (e.g. 3D printing), moulding, casting, precision lathes, CNC machining, etc.

In the implants of FIGS. 1 to 27, 60 and 61, the material for the pad can extend continuously from side-to-side, from front-to-back and from a pad top surface to a pad bottom surface. In other words, the one-and-same material that is employed for both the bracket and the pad defines a continuous intervertebral implant, including by providing continuity of support between adjacent vertebrae. When a suitable material is used, such an implant can be simply and easily formed (e.g. moulded or printed) and yet be robust and reliable.

The various intervertebral implant embodiments disclosed herein can:
- provide the opportunity to interconnect two or more than two vertebrae;
- provide greater flexibility and mobility to function operationally more closely to the natural spine;
- prove to be cost-effective and to adapt to variations in the shape and size of vertebrae in different patients;

provide greater mobility and stability of the respective vertebrae within the normal range of spinal movement (because of the integrated design and flexibility of the component parts and materials operationally functioning together as one);

provide less likelihood of lateral and other displacement and breakdown of component parts because of the operational flexibility and design of the component parts;

provide less likelihood over time of disc degeneration in adjacent segments of the spine because of the improved mobility of the treated vertebrae;

provide less wear and tear on the components of the implant because of its integrated overall flexibility resulting in its greater capacity to absorb stresses associated with normal movement of the spine;

provide less chance of dislodgement of the device within the intervertebral space or the loosening of fixing screws because of the intrinsic flexibility and greater capacity of the implant to absorb and minimise stresses from spinal movement;

offer greater capacity to conform to structural profiles of the different vertebrae and disc spaces and different clinical conditions of patients;

provide less chance of infection because of the flexible nature of the device to conform to variations in the shape and profile of different vertebrae and disc spaces and thereby close fix the implant with screws in position, possibly aided by adhesive, with minimum gaps;

provide less chance of infection because the pad location element virtually occupies the entire disc area of the vertebrae and therefore reduces the incidence of gaps and pockets where infection can start;

offer greater opportunity to provide a full range of implants to use in every segment of the spine (e.g. cervical to lumbar) which can prove to be cost-effective in surgical procedures and with reduced operating time;

provide pads/locators that can be moved along the connecting bracket so that the pad locators can be positioned to meet variations in the intervertebral disc spacing;

provide surface coatings on the surfaces of the pads/locators, such that there is a greater chance of new bone growth developing between the surfaces of the pad locators and the upper and lower surfaces of the respective vertebrae.

provide for the introduction of adhesive to cement the upper and lower surfaces of pads/locators to the upper and lower surfaces of vertebral bodies;

provide a variety of insert pads to achieve different performance characteristics depending on the segments of the spine to be treated and the needs of individual patients.

A non-limiting example of a surgical methodology deploying an embodiment of the device will now be provided.

Example

In one example of a surgical procedure, an intervertebral disc implant device in the form of a single bracket and pad, such as those set forth in embodiment 1, was deployed between two selected and adjacent vertebrae in the spinal column.

In this procedure, the degenerated intervertebral disc was first surgically removed from the spinal column of the patient, before inserting the bracket and pad.

Firstly the surgeon supported the two selected and adjacent vertebrae of the patient, using suitable clamping and jigs. The surgeon then removed the degenerated natural disc from between the two supported vertebrae using suitable surgical implements.

Once the area was clean/clear of the natural disc, the surgeon inserted into the intervertebral disc space the pad between the two adjacent vertebrae. Once the pad was in a suitable location, the surgeon secured opposite ends of the bracket to respective anterior faces of the adjacent two vertebrae, using one (or more) surgical screws at each end of the bracket connector.

Depending on the type of bracket deployed, the surgeon was able to make in situ adjustments during deployment, and optionally to thereafter inject adhesive cement and/or bone growth promoter to help secure the pad to the adjacent two vertebrae.

For a dual (or multiple) disc bracket, the above procedure was repeated, except that two (or more) degenerated discs and the three (or more) respective and adjacent vertebrae were immobilized and cleaned/cleared. Then, a suitable multi-bracket was deployed into the two (or more) cleared intervertebral disc spaces, optionally with in situ adjustments during deployment, and optionally with adhesive cement and/or bone growth promoter introduction.

Whilst specific embodiments of an intervertebral disc implant device, and a method of deploying the device, have been described, it should be appreciated that the device and surgical procedure may be embodied in other forms.

In the claims which follow, and in the preceding description, except where the context requires otherwise due to express language or necessary implication, the word "comprise" and variations such as "comprises" or "comprising" are used in an inclusive sense, i.e. to specify the presence of the stated features but not to preclude the presence or addition of further features in various embodiments of the intervertebral disc implant device and method as disclosed herein.

The invention claimed is:

1. A customized, patient specific intervertebral disc replacement device configured to replace one or more intervertebral discs in a spinal column of a human or an animal to restore or provide flexibility and mobility post-operatively to at least two adjacent vertebrae, the device configured to be positioned with respect to at least one intervertebral disc space respectively located between the at least two adjacent vertebrae, the device comprising:
   a connector integrally formed with at least one shock absorbing pad, the connector configured to extend between and interconnect the at least two adjacent vertebrae when the at least one shock absorbing pad is located within the at least one intervertebral disc space;
   wherein the at least one shock absorbing pad is made from the same material as the connector such that the at least one shock absorbing pad extends laterally from the connector, wherein the material of the connector and the at least one shock absorbing pad is continuous from side-to-side, from front-to-back and from a pad top surface to a pad bottom surface, and wherein the material of the connector and the at least one shock absorbing pad is a compressible, flexible, and resilient biocompatible material selected from the group consisting of compressible polymers, silicon-based flexible polymers, elastomers, and elasto-plastics,
   wherein the at least one shock absorbing pad is configured to exhibit mechanical and functional properties similar to those of a natural biological intervertebral disc such that the at least one shock absorbing pad is configured to simulate similar mobility, operational function and normal performance of the natural biological intervertebral disc, and wherein the at least one shock absorbing pad is configured to be customized to and made specifically for an individual patient based on anatomical characteristics of the individual patient's intervertebral disc space by molding, 3D printing from digitized MRI, or other radiographic techniques, so that the at least one shock absorbing pad is configured to fill the entire at least one intervertebral disc space from side-to-side, front-to-back and top-to-bottom upon being deployed and located therein.

2. The intervertebral disc replacement device as recited in claim 1, wherein the connector further comprises a reinforcing element extending therethrough.

3. The intervertebral disc replacement device as recited in claim 2, wherein the reinforcing element also extends through the at least one shock absorbing pad.

4. The intervertebral disc replacement device as recited in claim 2, wherein the reinforcing element comprises a relatively rigid, bendable material.

5. The intervertebral disc replacement device as recited in claim 4, wherein the reinforcing element material is metal.

6. The intervertebral disc replacement device as recited in claim 1, wherein the connector is elongate and is configured at or adjacent to opposing ends thereof to be secured to anterior surfaces of the at least two adjacent vertebrae.

7. The intervertebral disc replacement device as recited in claim 6, wherein the connector is configured at or adjacent to its opposing ends to be screwed or pinned to the anterior surfaces of the at least two adjacent vertebrae.

8. The intervertebral disc replacement device as recited in claim 1, wherein the connector is elongate and configured to span at least three adjacent vertebrae.

9. The intervertebral disc replacement device as recited in claim 8, wherein the connector is configured to be secured to anterior surfaces of each of the at least three adjacent vertebrae.

10. The intervertebral disc replacement device as recited in claim 8, wherein the device comprises a shock absorbing pad for each of the intervertebral disc spaces that are respectively located between the at least three adjacent vertebrae.

11. The intervertebral disc replacement device as recited in claim 1, wherein the at least one shock absorbing pad is disc-shaped.

12. A surgical procedure for replacement of at least one degenerated natural intervertebral disc, the procedure comprising inserting the at least one shock absorbing pad of the intervertebral disc replacement device as set forth in claim 1 between at least two selected and adjacent vertebrae of a patient and securing opposing ends of the connector to respective anterior faces of the at least two vertebrae.

* * * * *